(12) United States Patent
Hoshi et al.

(10) Patent No.: US 8,389,711 B2
(45) Date of Patent: Mar. 5, 2013

(54) PHARMACEUTICAL COMPOSITION FOR TREATMENT OF CANCER AND ASTHMA

(75) Inventors: Hirotaka Hoshi, Tokyo (JP); Motoyuki Uchida, Tokyo (JP); Hikaru Saito, Tokyo (JP)

(73) Assignee: Kureha Corporation, Tokyo (JP)

( * ) Notice: Subject to any disclaimer, the term of this patent is extended or adjusted under 35 U.S.C. 154(b) by 0 days.

(21) Appl. No.: 13/139,280

(22) PCT Filed: Dec. 14, 2009

(86) PCT No.: PCT/JP2009/070812
§ 371 (c)(1),
(2), (4) Date: Jun. 10, 2011

(87) PCT Pub. No.: WO2010/067882
PCT Pub. Date: Jun. 17, 2010

(65) Prior Publication Data
US 2011/0245325 A1    Oct. 6, 2011

(30) Foreign Application Priority Data

Dec. 12, 2008  (JP) ................................ 2008-317712
Dec. 12, 2008  (JP) ................................ 2008-317713

(51) Int. Cl.
    *C07H 21/04*    (2006.01)
(52) U.S. Cl. .................. 536/24.5; 536/24.31; 536/24.1; 514/44; 435/6; 435/325; 435/375
(58) Field of Classification Search ........................ None
    See application file for complete search history.

(56) References Cited

U.S. PATENT DOCUMENTS

| 2003/0143732 A1* | 7/2003 | Fosnaugh et al. ............. 435/325 |
| 2004/0002077 A1* | 1/2004 | Taira et al. ........................ 435/6 |
| 2004/0259247 A1* | 12/2004 | Tuschl et al. ................... 435/375 |
| 2006/0150262 A1 | 7/2006 | Bienkowska et al. |

OTHER PUBLICATIONS

Jinfeng, et al.; Expression of MUC5AC and MUC6 in Invasive Ductal Carcinoma of the Pancreas and Relationship with Prognosis; Int. Journal of Gastrointestinal Cancer; 2003; vol. 34, No. 1, 9-18.
Yamasaki, et al.; Expression and localization of MUC1, MUC2, MUC5AC and small intestinal mucin antigen in pancreatic tumors; *International Journal of Oncology*; 2004; pp. 107-113; vol. 24; Greece.
Arakawa, et al.; Role of Mucus Hyper-Secretion and its Regulation in Bronchial Asthma; *The Japanese Journal of Pediatric Allergy and Clinical Immunology*; 2007; pp. 180-186; vol. 21; Japan (English abstract included).
Iacobuzio-Donahue, et al.; Highly Expressed Genes in Pancreatic Ductal Adenocarcimonas: A Comprehensive Characterization and Comparison of the Transcription Profiles Obtained from Three Major Technologies; *Cancer Res.*; 2003; pp. 8614-8622; vol. 63.

Ordoñez, et al.; Mild and Moderate Asthma is Associated with Airway Goblet Cell Hyperplasia and Abnormalities in Mucin Gene Expression;*Am. J. Respir. Crit. Care Med.*; 2001; pp. 517-523; vol. 163, No. 2.
Database DDBJ/EMBL/GenBank; Accession No. NM_017511; Jun. 15, 2008; http://www.ncbi.nlm.nih,gov/sviewer/viewer.fcgi?161019169:NCBI:23039180>.
Chaturvedi, P. et al., "MUC4 Mucin Potentiates Pancreatic Tumor Cell Proliferation, Survival, and Invasive Properties and Interferes with Its Interaction to Extracellular Matrix Proteins", *Molecular Cancer Research*, vol. 5, No. 4, Apr. 1, 2007, pp. 309-320, XP55035583, ISSN: 1541-7786, DOI: 10.1158/1541-7786.MCR-06-0353.
Hoshi, H. et al., "Tumor-associated MUC5AC stimulates in vivo tumorigenicity of human pancreatic cancer", *International Journal of Oncology*, vol. 38, No. 3, Mar. 1, 2011, XP55035579, ISSN: 1019-6439, DOI: 10.3892/ijo.2011.911.
Ohuchida, K. et al., "Quantitative analysis of MUC1 and MUC5AC mRNA in pancreatic juice for preoperative diagnosis of pancreatic cancer", *International Journal of Cancer*, vol. 118, No. 2, Jan. 15, 2006, pp. 405-411, XP55035585, ISSN: 0020-7136, DOI: 10.1002/ijc.21317.
Wang, Y. et al., "Diagnostic value of mucins (MUC1, MUC2 and MUC5AC) expression profile in endoscopic ultrasound-guided fine-needle aspiration specimens of the pancreas", *International Journal of Cancer*, vol. 121, No. 12, Dec. 15, 2007, pp. 2716-2722, XP55035584. ISSN: 0020-7136, DOI: 10.1002/ijc.22997, Changhai Hospital, Second Military Medical University, Shanghai, China.
Yamazoe, S. et al., "RNA interference suppression of mucin 5AC (MUC5AC) reduces the adhesive and invasive capacity of human pancreatic cancer cells", *Journal of Experimental & Clinical Cancer Research*, Biomed Central Ltd., London UK, vol. 29, No. 1, May 23, 2010, p. 53, XP021083460, ISSN: 1756-9966, DOI: 10.1186/1756-9966-29-53.
Yuan, Z. et al., "MUC1 Knockdown With RNA Interference Inhibits Pancreatic Cancer Growth", *Journal of Surgical Research*, Academic Press Inc., San Diego, CA, US, vol. 157, No. 1, Oct. 7, 2008, pp. e39-e46, XP026694396, ISSN: 0022-4804, DOI:10.1016/J.JSS.2008.09.005 [retrieved on Oct. 15, 2009].

* cited by examiner

*Primary Examiner* — Kimberly Chong
(74) *Attorney, Agent, or Firm* — Kilpatrick Townsend & Stockton LLP

(57) ABSTRACT

Provided is a pharmaceutical composition for treating cancer and asthma.
The object can be solved by a pharmaceutical composition comprising a siRNA molecule that directs cleavage of mRNA of mucin subtype 5 AC via RNA interference, or an antibody against mucin subtype 5AC as an active ingredient. According to the pharmaceutical composition of the present invention, diseases involving an overexpression of mucin subtype 5 AC can be treated efficiently. In particular, the pharmaceutical composition comprising a siRNA molecule of the present invention is effectively used in the treatment of a cancer, particularly pancreatic cancer. In addition, the siRNA or the antibody of the present invention can inhibit the expression or function of MUC5AC, thereby preventing or treating the symptoms of asthma effectively.

16 Claims, 4 Drawing Sheets a Control IgG
b Anti-MUC5AC antibody
c Anti-EGFR antibody
d Without primary antibody Mouse serum injected
with mock line
(MUC5AC expression)

Mouse serum injected
with si line
(MUC5AC non-expression)

PHARMACEUTICAL COMPOSITION FOR TREATMENT OF CANCER AND ASTHMA

CROSS-REFERENCE TO RELATED APPLICATIONS

The present application is a National Stage application under 35 U.S.C. §371, claiming priority to PCT/JP09/070,812, filed Dec. 14, 2009, which application claims the benefit of priority to Japanese Patent Application No. 2008-317712, filed Dec. 12, 2008, and Japanese Patent Application No. 2008-317713, filed Dec. 12, 2008, the teachings of which are incorporated herein by reference in their entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 28313-14.TXT, created on Mar. 6, 2012, 16,384 bytes, machine format IBM-PC, MS-Windows operating system, is hereby incorporated by reference in its entirety for all purposes.

TECHNICAL FIELD

The present invention relates to a small interfering RNA (siRNA) molecule that is specific to mucin subtype 5AC (hereinafter, sometimes referred to as "MUC5AC"), and a pharmaceutical composition containing the same. According to the siRNA molecule of the present invention, it is possible to effectively treat cancer and asthma by specific suppression of MUC5AC expression.

BACKGROUND ART

Mucin is a glycoprotein in which a core protein is modified with a high-molecular-weight sugar chain. The high-molecular-weight sugar chain is a macromolecule having 100 to 10 million of the molecular weight. Mucin is found as a sticky substance in the mucosal membrane of the oral cavity, respiratory tract, stomach, or intestinal tract of an animal, and protects a tender mucosal membrane in an inner cavity that is in contact with the outside, from pathogens, foreign substances, drying, and the like. Twenty-one kinds of mucin are known in humans, and core proteins of each of the mucin molecules have different repeat sequences. The region of the repeat amino acid sequence contains an abundance of serine and threonine, and a mucin-type sugar chain is bound thereto in high frequency. The mucin-type sugar chain is generally composed of N-acetyl galactosamine, N-acetyl glucosamine, galactose, fucose, sialic acid, or the like. The sugar chain contributes 50 to 80% or more of the molecular weight of mucin, and is a cause of diverse properties of mucin, such as stickiness, water retention ability, resistance to a protein degrading enzymes and the like.

Among the mucins, MUC5AC has a repeat sequence that is abundant in serine and threonine as a core protein. In normal tissue, MUC5AC is expressed only in epithelial cells of the trachea or stomach. Regarding the relationship of the MUC5AC and diseases, it is known that MUC5AC is expressed in cancer tissue. In particular, it is reported that MUC5AC, which is a membrane-binding type mucin, is expressed at a high rate in association with canceration of the pancreas (Non-patent literatures 1 and 2). In addition, it is reported that excessive secretion of MUC5AC in the respiratory tract leads to aggravation of asthma in patients with asthma (Non-patent literature 3).

Pancreatic cancer is known as a refractory cancer. In 2000, the number of patients with cancer of the pancreas was 17,000 in Japan, and 30,000 in the US. The number of pancreatic cancer patients is predicted to increase. Pancreatic cancer patients do not make up a large proportion of cancer patients. However, the degree of malignancy, which is a number of age-adjusted death rate divided with age-adjusted cancer rate, of pancreatic cancer was the highest among all cancers in 1998. That is, the degree of malignancy was 99.2% for men and 94.6% for women. In addition, the 5-year-survival rate of the pancreatic cancer patients is very low (approximately 10%) in both men and women, which means that pancreatic cancer is a refractory cancer having a poor prognosis.

A current standard therapy for pancreatic cancer is surgery. That is, in the case of early diagnosis, removal of tumor site is considered to be an effective therapy. However, pancreatic cancer has few symptoms, and so diagnosis of early lesions (1 cm or less) using an endoscope or diagnostic imaging is difficult. Furthermore, a tumor marker specific to pancreatic cancer does not exist. Therefore, it is difficult to detect pancreatic cancer in its early stages, and only about 30% of cases allow operation. For advanced-staged pancreatic cancer, a chemical therapy is mainly conducted. In particular, gemcitabine (nucleic acid synthesis inhibitor, Eli Lilly Japan K.K.) is used. However, this only has symptom alleviation effects, and has no fundamental therapeutic effects on the tumor. Sometimes, a radiation therapy is combined with the surgical therapy. However, pancreatic cancer has low sensitivity to radiation, and this therapy is not effective. Therefore, it is desirable to develop an effectual pharmaceutical composition capable of suppressing the proliferation of tumor cells and improving the QOL in pancreatic cancer patients.

As described above, MUC5AC is expressed at a high rate in tissue of pancreatic cancer. However, it is reported that lymph invasion, blood vessel invasion, and lymph node metastasis are found in pancreatic cancer patients having no expression of MUC5AC, and therefore, the survival rate is better in pancreatic cancer patients having MUC5AC expression (Non-patent literature 1). Accordingly, from a viewpoint of the survival rate of pancreatic cancer patients, it is preferable that MUC5AC is expressed in pancreatic cancer.

CITATION LIST

Non-Patent Literature

[Non-patent literature 1] International Journal of Gastrointestinal Cancer) (the United state) 2003, vol. 34, p. 9-18
[Non-patent literature 2] International Journal of Oncology (Greece) 2004, vol. 24, p. 107-113
[Non-patent literature 3] "Zensoku ni Okeru Bunpi to sono Seigyo (Nihon Shoni Arerugi Gakkaishi; The Japanese Journal of Pediatric Allergy and Clinical Immunology)" (Japan) 2007, vol. 21, p. 180-186

SUMMARY OF INVENTION

Technical Problem

The present inventors have conducted intensive studies into an effectual pharmaceutical composition that can suppress proliferation of cancer cells in vivo, and as a result, found that a siRNA that targets the mRNA of MUC5AC can suppress proliferation of pancreatic cancer cells expressing MUC5AC in vivo, and sometimes significantly suppress metastasis of pancreatic cancer. In other words, the present inventors have found that cancer proliferation can be suppressed by knock-down of MUC5AC, even though it was thought that expression of MUC5AC is advantageous to pancreatic cancer from a viewpoint of survival rate of pancreas cancer patients from the above-mentioned Non-patent literature 1. The siRNA molecule of the present invention can induce effective immune response to cancer cells in cancer patients, and for example, can induce: production of antibodies for cancer cells by B cell, invasion of leucocytes (for example, B cell, or granulocyte) into a cancer tissue, cytotoxic activity of mononuclear cells or polynuclear cells against cancer cells. That is, the present inventors have found that a pharmaceutical composition containing siRNA for MUC5AC is useful as a medicine for treating cancer, particularly pancreatic cancer. Furthermore, the present inventors have found that the siRNA molecule of the present invention is useful in improvement of symptoms of asthma in patients with asthma.

The present invention is based on the above findings.

Solution to Problem

The present invention relates to a small interfering RNA (siRNA) molecule that directs cleavage of mRNA of mucin subtype 5 AC via RNA interference.

According to a preferable embodiment of the siRNA of the present invention, the target mRNA region of the RNA interference is selected from the group consisting of: an mRNA region consisting of a nucleotide sequence of SEQ ID No. 1, an mRNA region consisting of a nucleotide sequence of SEQ ID No. 3, an mRNA region consisting of a nucleotide sequence of SEQ ID No. 5, an mRNA region consisting of a nucleotide sequence of SEQ ID No. 7, an mRNA region consisting of a nucleotide sequence of SEQ ID No. 9, an mRNA region consisting of a nucleotide sequence of SEQ ID No. 11, an mRNA region consisting of a nucleotide sequence of SEQ ID No. 16, and an mRNA region consisting of a nucleotide sequence of SEQ ID No. 21.

According to a preferable embodiment of the siRNA of the present invention, the siRNA has a double-stranded RNA of 15 to 40 nucleotides in length.

According to a preferable embodiment of the siRNA of the present invention, the antisense RNA of the double-stranded RNA section comprises an RNA section consisting of a nucleotide sequence complementary to the nucleotide sequence of the target mRNA region, or an RNA section consisting of a nucleotide sequence in which any one of 1 to 9 nucleotides are deleted, substituted, and/or added in one or more portions of the nucleotide sequence complementary to the nucleotide sequence of the target mRNA region. More preferably, the antisense RNA of the double-stranded RNA section comprises an RNA section consisting of the sequential nine or more nucleotide sequence in the nucleotide sequence complementary to the nucleotide sequence of the target mRNA region.

The present invention also relates to the siRNA molecule as above, wherein the antisense RNA of the double-stranded RNA section is selected from the group consisting of: an RNA consisting of a nucleotide sequence of SEQ ID No. 2, an RNA consisting of a nucleotide sequence of SEQ ID No. 4, an RNA consisting of a nucleotide sequence of SEQ ID No. 6, an RNA consisting of a nucleotide sequence of SEQ ID No. 8, an RNA consisting of a nucleotide sequence of SEQ ID No. 10, an RNA consisting of a nucleotide sequence of SEQ ID No. 12, an RNA consisting of a nucleotide sequence of SEQ ID No. 17, and an RNA consisting of a nucleotide sequence of SEQ ID No. 22.

According to a preferable embodiment of the siRNA of the present invention, the siRNA is:
(a) a shRNA in which the two RNA strands constituting the double-stranded RNA section are connected with a RNA section which is capable of forming a hairpin loop,
(b) a double-stranded nucleotide the ends of which are blunt ends, or
(c) a double-stranded nucleotide in which the one or two ends thereof are protruding ends that are attached to a deoxyribonucleotide or a ribonucleotide on one or both 3'-ends of the two RNA strands constituting the double-stranded RNA section.

The present invention also relates to a DNA comprising: a DNA section encoding the siRNA molecule as above, a promoter region at the 5'-terminus of the DNA section which is capable of controlling transcription of the DNA section, and a terminator region at the 3'-terminus of the DNA section; and a vector comprising the DNA.

Further, the present invention relates to a pharmaceutical composition comprising, as an active ingredient, at least one component selected from the group consisting of the above siRNA molecule, the above DNA, and the above vector.

According to a preferable embodiment of the pharmaceutical composition of the present invention, it is one for treating a disease involving an overexpression of mucin subtype 5 AC. According to a preferable embodiment of the pharmaceutical composition of the present invention, the disease involving an overexpression of mucin subtype 5 AC is cancer or asthma, more preferably, the cancer is pancreatic cancer, lung cancer, breast cancer, stomach cancer, cervical cancer, or large intestine cancer.

The present invention relates to a method for treating a disease involving an overexpression of mucin subtype 5 AC, comprising administrating to a patient in need of such treatment a therapeutically effective amount of at least one component selected from the group consisting of the above siRNA molecule, the above DNA, and the above vector.

According to a preferable embodiment of the method for treating a disease of the present invention, the disease involving an overexpression of mucin subtype 5 AC is cancer or asthma, more preferably, the cancer is pancreatic cancer, lung cancer, breast cancer, stomach cancer, cervical cancer, or large intestine cancer.

The present invention relates to the siRNA molecule as above, for treatment of a disease involving an overexpression of mucin subtype 5 AC. According to a preferable embodiment of the siRNA molecule for treatment of the present invention, the disease involving an overexpression of mucin subtype 5 AC is cancer or asthma, more preferably, the cancer is pancreatic cancer, lung cancer, breast cancer, stomach cancer, cervical cancer, or large intestine cancer.

The present invention relates to the DNA, for treatment of a disease involving an overexpression of mucin subtype 5 AC. According to a preferable embodiment of the DNA for treatment of the present invention, the disease involving an overexpression of mucin subtype 5 AC is cancer or asthma, more preferably, the cancer is pancreatic cancer, lung cancer, breast cancer, stomach cancer, cervical cancer, or large intestine cancer.

The present invention relates to the vector, for treatment of a disease involving an overexpression of mucin subtype 5 AC. According to a preferable embodiment of the vector for treatment of the present invention, the disease involving an overexpression of mucin subtype 5 AC is cancer or asthma, more preferably, the cancer is pancreatic cancer, lung cancer, breast cancer, stomach cancer, cervical cancer, or large intestine cancer.

The present invention relates to a use of at least one component selected from the group consisting of: the above siRNA molecule, the above DNA, and the above vector, for the manufacture of a medicament for treatment of a disease involving an overexpression of mucin subtype 5 AC.

According to a preferable embodiment of the use of the present invention, the disease involving an overexpression of mucin subtype 5 AC is cancer or asthma, more preferably, the cancer is pancreatic cancer, lung cancer, breast cancer, stomach cancer, cervical cancer, or large intestine cancer.

Further, the present invention relates to a cell wherein a gene expression of mucin subtype 5 AC is knocked down by the siRNA molecule defined as above.

The present invention relates to a method for screening an agent, using a cell wherein a gene expression of mucin subtype 5 AC is knocked down by the siRNA molecule defined as above, and a cell wherein a gene of mucin subtype 5 AC is expressed.

According to a preferable embodiment of the screening method of the present invention, the agent is an anticancer agent or an antiasthma agent.

The term "siRNA" as used herein means a small interfering RNA. The siRNA comprises at least a double-stranded RNA section, and induces a sequence-specific inhibition of gene expression i.e. RNA interference (RNAi). A mRNA targeted by siRNA is destroyed by the RNA interference, whereby a expression of protein encoded by the mRNA is suppressed.

Advantageous Effects of Invention

According to the siRNA molecule of the present invention, it is possible to effectively treat diseases involving an overexpression of MUC5AC. Particularly, it is possible to effectively suppress proliferation of cancer cells in vivo in which MUC5AC are excessively expressed. The pharmaceutical composition containing the siRNA molecule of the present invention can be effectively used in treatment of cancers, particularly in pancreatic cancer in which MUC5AC is expressed. In addition, the siRNA molecule of the present invention can effectively suppress expression of MUC5AC in cells of the bronchial tube in which MUC5AC is expressed. In asthma patients, the siRNA molecule of the present invention can effectively prevent or treat symptoms of asthma by suppressing MUC5AC expression.

DESCRIPTION OF EMBODIMENTS

Figure 1:
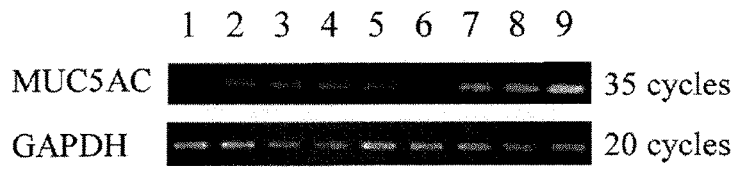
FIG. 1 is a photograph of electrophoresis showing the genetic expression of MUC5AC in SW1990 cells which are transfected with the oh-siRNA1 to oh-siRNA8 and cultured for 48 hours. The expression of GAPDH was examined as a positive control. (lane 1: oh-siRNA1, lane 2: oh-siRNA2, lane 3: oh-siRNA3, lane 4: oh-siRNA4, lane 5: oh-siRNA5, lane 6: oh-siRNA6, lane 7: oh-siRNA7, lane 8: oh-siRNA8, lane 9: untransfected SW1990 cells)

Hereinafter, the present invention will be explained in detail.

1. siRNA, DNA, and Vector of the Present Invention

The siRNA molecule of the present invention is not limited as long as it has a double-stranded RNA section, and directs cleavage of mRNA of MUC5AC via RNA interference. However, siRNA capable of directing cleavage, via RNA interference, of a target mRNA region 1 consisting of a nucleotide sequence represented by SEQ ID No. 1, a target mRNA region 2 consisting of a nucleotide sequence represented by SEQ ID No. 3, a target mRNA region 3 consisting of a nucleotide sequence represented by SEQ ID No. 5, a target mRNA region 4 consisting of a nucleotide sequence represented by SEQ ID No. 7, a target mRNA region 5 consisting of a nucleotide sequence represented by SEQ ID No. 9, a target mRNA region 6 consisting of a nucleotide sequence represented by SEQ ID No. 11, a target mRNA region 7 consisting of a nucleotide sequence represented by SEQ ID No. 16, or a target mRNA region 8 consisting of a nucleotide sequence represented by SEQ ID No. 21, which are mRNAs of MUC5AC, is preferable. The most preferable target mRNA region is the target mRNA region 6. The base sequences of the nucleotides of the target mRNA regions are shown in Table 1.

TABLE 1

| Name | Base sequence |
| --- | --- |
| Target mRNA region 1 | G G A G C C U G A U C A U C C A G C A<br>(SEQ ID No. 1) |
| Target mRNA region 2 | G C A G G C A C U U C U C C A G G A<br>(SEQ ID No. 3) |
| Target mRNA region 3 | G C A G U G C C U U C A C U G U A C U<br>(SEQ ID No. 5) |
| Target mRNA region 4 | A C A C C A A G C U G A C A C C C A U<br>(SEQ ID No. 7) |
| Target mRNA region 5 | C C C U C A A C C U U C U U C A U C A<br>(SEQ ID No. 9) |
| Target mRNA region 6 | U U U G A G A G A C G A A G G A U A C<br>(SEQ ID No. 11) |
| Target mRNA region 7 | G G A A A C C U A C A A C A A C A U C<br>(SEQ ID No. 16) |
| Target mRNA region 8 | C A U C A A C A U C A U C C A U G U C<br>(SEQ ID No. 21) |

In addition, several splicing variants of the MUC5AC mRNAs due to the differences of the processings, are known (GenBank Accession No.: NM 017511, XM 001714774, NM_001134429, NM_001714104). If each of the variants has the above-mentioned target mRNA regions, the siRNA molecule of the present invention can direct cleavage of mRNA via RNA interference.

The double-stranded RNA section has 15 to 40 nucleotides, preferably 15 to 30 nucleotides, more preferably 15 to 25 nucleotides, further preferably 19 to 25 nucleotides, and most preferably 19 to 21 nucleotides. The double-stranded RNA section comprises those functioning as siRNA per se. In addition, the double-stranded RNA section may comprise those that are cleaved by Dicer in a cell to induce RNA interference as siRNA.

The antisense RNA of the double-stranded RNA is not limited as long as it can be hybridized to mRNA of MUC5AC in a cell. It may be RNA including a RNA section consisting of a nucleotide sequence in which 1 to 9, preferably 1 to 5, more preferably 1 to 3, most preferably 1 nucleotide is deleted, substituted, or added in the nucleotide sequence of the RNA section consisting of the nucleotide sequence complementary to the nucleotide sequence of the target mRNA region (hereinafter, referred to as the target-complementary RNA section), and/or a RNA section consisting of a nucleotide sequence of at least 9 consecutive nucleotides, preferably at least 10 consecutive nucleotides, more preferably at least 15 consecutive nucleotides or most preferably at least 19 consecutive nucleotides of the above-mentioned target complementary RNA section nucleotide sequence. The antisense RNA sequence of the double-stranded RNA is preferably a RNA strand including a RNA section consisting of a nucleotide sequence represented by SEQ ID No. 2 (siRNA-1as), a RNA section consisting of a nucleotide sequence represented by SEQ ID No. 4 (siRNA-2as), a RNA section consisting of a nucleotide sequence represented by SEQ ID No. 6 (siRNA-3as), a RNA section consisting of a nucleotide sequence represented by SEQ ID No. 8 (siRNA-4as), a RNA section consisting of a nucleotide sequence represented by SEQ ID No. 10 (siRNA-5as), a RNA section consisting of a nucleotide sequence represented by SEQ ID No. 12 (siRNA-6as), a RNA section consisting of a nucleotide sequence represented by SEQ ID No. 17 (siRNA-7as), or a RNA section consisting of a nucleotide sequence represented by SEQ ID No. 22 (siRNA-8as), each of which is completely complementary to each of the target mRNA regions 1 to 8 of mRNA of MUC5AC. Most preferably, the antisense RNA sequence of the double-stranded RNA is a RNA strand consisting of siRNA-6as. Each of the nucleotide sequences are shown in Table 2.

TABLE 2

| Name | Base sequence |
| --- | --- |
| siRNA-1as | U G C U G G A U G A U C A G G C U C C<br>(SEQ ID No. 2) |
| siRNA-2as | U C C U G G G A G A A G U G C C U G C<br>(SEQ ID No. 4) |
| siRNA-3as | A G U A C A G U G A A G G C A C U G C<br>(SEQ ID No. 6) |
| siRNA-4as | A U G G G U G U C A G C U U G G U G U<br>(SEQ ID No. 8) |
| siRNA-5as | U G A U G A A G A A G G U U G A G G G<br>(SEQ ID No. 10) |

TABLE 2-continued

| Name | Base sequence |
|---|---|
| siRNA-6as | G U A U C C U U C G U C U C U C A A A (SEQ ID No. 12) |
| siRNA-7as | G A U G U U G U U G U A G G U U U C C (SEQ ID No. 17) |
| siRNA-8as | G A C A U G G A U G A U G U U G A U G (SEQ ID No. 22) |

The antisense RNA sequence can contain a RNA section in addition to the above-mentioned target-complementary RNA section. This additional RNA section is not particularly limited, but is preferably a RNA section that is of mRNA of MUC5AC, and consists of a nucleotide sequence complementary to the nucleotide sequence of mRNA of MUC5AC other than the target mRNA regions.

In addition, the nucleotide sequence of the antisense RNA strand has 85%, preferably 90%, more preferably 95%, and most preferably 100% homology with the nucleotide sequence of the target mRNA region. In addition, the antisense RNA section is preferably designed such that the GC content of total siRNA is 70% or less, preferably 30 to 70%, or about 30 to 60%.

The sense RNA sequence of the double-stranded RNA section is not limited as long as it is RNA that can be hybridized with the antisense RNA sequence within a cell. For example, the sense RNA sequence of the double-stranded RNA section may be a RNA strand consisting of a nucleotide sequence in which 1 to 9, preferably 1 to 5, more preferably 1 to 3 or most preferably 1 nucleotide is deleted, substituted, or added in a nucleotide sequence consisting of a nucleotide sequence complementary to the nucleotide sequence of the antisense RNA. Most preferably the sense RNA sequence consists of a nucleotide sequence completely complementary to the nucleotide sequence of the antisense RNA.

In addition, the sense RNA sequence may contain a RNA section consisting of a nucleotide sequence in which 1 to 9, preferably 1 to 5, more preferably 1 to 3, or most preferably 1 nucleotide is deleted, substituted, or added in the nucleotide sequence of the above-mentioned target mRNA region (hereinafter, the "RNA of the sense RNA sequence" is sometimes simply referred to as the "target RNA section"), and/or a RNA section consisting of a nucleotide sequence of at least 9 consecutive nucleotides, preferably at least 10 consecutive nucleotides, more preferably at least 15 consecutive nucleotides, most preferably at least 19 consecutive nucleotides in the nucleotide sequence of the above-mentioned target RNA section. However, the sense RNA sequence of the double-stranded RNA section preferably contains a RNA section consisting of one of the nucleotide sequences of the above-mentioned target mRNA regions 1 to 8, i.e. the nucleotide sequences represented by SEQ ID No. 1, SEQ ID No. 3, SEQ ID No. 5, SEQ ID No. 7, SEQ ID No. 9, SEQ ID No. 11, SEQ ID No. 16, and SEQ ID No. 21 (hereinafter, referred to as siRNA-1s, siRNA-2s, siRNA-3s, siRNA-4s, siRNA-5s, siRNA-6s, siRNA-7s, and siRNA-8s, respectively) in the mRNA of MUC5AC, and most preferably a RNA strand consisting of siRNA-6s. Each of the nucleotide sequences is shown in Table 3.

TABLE 3

| Name | Base sequence |
|---|---|
| siRNA-1s | G G A G C C U G A U C A U C C A G C A (SEQ ID No. 1) |
| siRNA-2s | G C A G G C A C U U C U C C C A G G A (SEQ ID No. 3) |
| siRNA-3s | G C A G U G C C U U C A C U G U A C U (SEQ ID No. 5) |
| siRNA-4s | A C A C C A A G C U G A C A C C C A U (SEQ ID No. 7) |
| siRNA-5s | C C C U C A A C C U U C U U C A U C A (SEQ ID No. 9) |
| siRNA-6s | U U U G A G A G A C G A A G G A U A C (SEQ ID No. 11) |
| siRNA-7s | G G A A A C C U A C A A C A A C A U C (SEQ ID No. 16) |
| siRNA-8s | C A U C A A C A U C A U C C A U G U C (SEQ ID No. 21) |

In addition, the sense RNA strand may contain a RNA section other than the above-mentioned target RNA section, and such RNA section is not particularly limited, but is preferably a RNA section that is a mRNA of MUC5AC and consists of a nucleotide sequence of mRNA of MUC5AC other than the target mRNA region.

The siRNA molecule of the present invention encompasses a double-stranded nucleotide that has smooth ends of a double-stranded RNA section, which is one embodiment of the present invention, and such siRNA shows sufficient RNAi activity.

In addition, the siRNA molecule of the present invention also encompasses a double-stranded oligonucleotide, which has protruding ends, that consists of a double-stranded RNA section and an overhang of the 3' end of a sense strand and/or antisense strand, which is one embodiment of the present invention. The above-mentioned overhang section is any nucleotide of 5 nucleotides or less (ribonucleotide or deoxyribonucleotide), but is preferably a nucleotide of 2 nucleotides. As the ribonucleotide consisting of the 3' end overhang of the siRNA, for example, nucleotides of u (uridine), a (adenosine), g (guanosine), or c (cytidine) may be used. As the deoxyribonucleotide consisting of the 3' end overhang, for example, nucleotides of dt (thymidine), da (deoxyadenosine), dg (deoxyguanosine), or do (deoxycytidine) may be used.

The above overhang is preferably an overhang in which 1 or 2 nucleotides of u or dt are added independently from each other at the 3' end of the sense strand and/or the antisense strand, more preferably an overhang in which 1 or 2 nucleotides of u or dt are added independently from each other at the 3' end of the sense strand and the antisense strand, and particularly preferably an overhang in which 2 nucleotides of u or dt are added independently from each other at the 3' end of the sense strand and the antisense strand. Furthermore, specific examples of the overhang include nucleotide sequences such as ug-3', uu-3', tg-3' and tt-3'. Accordingly, examples of the overhang double-stranded siRNA include overhang double-stranded siRNAs obtained by annealing of a nucleotide in which tt-3' is added to the 3' end of the siRNA-1s to the siRNA-8s, and a nucleotide in which tt-3' is added to the 3' end of the siRNA-las to the siRNA-8 as. Specific examples of the overhang double-stranded siRNA include those obtained by annealing GGAGCCUGAUCAUCCAGCAtt (SEQ ID NO:31) and UGCUGGAUGAUCAGGCUCCtt (SEQ ID NO:32) (oh-siRNA1), those obtained by annealing GCAGGCACUUCUCCCAGGAtt (SEQ ID NO:33) and UCCUGGGAGAAGUGCCUGCtt (SEQ ID NO:34) (oh-siRNA2), those obtained by annealing GCAGUGCUUCACUGUACUtt (SEQ ID NO:35) and AGUACAGUGAAGCACUGCtt (SEQ ID NO:36) (oh-siRNA3), those obtained by annealing ACACCAAGCUGACACCCAUtt (SEQ ID NO:37) and AUGGGUGUCAGCUUGGUGUtt (SEQ ID NO:38) (oh-siRNA4), those obtained by annealing CCCUCAACCUUCUUCAUCAtt (SEQ ID NO:39) and UGAUGAAGAAGGUUGAGGGtt (SEQ ID NO:40) (oh-siRNA5), those obtained by annealing UUUGAGAGACGAAGGAUACtt (SEQ ID NO:41) and GUAUCCUUCGUCUCUCAAAtt (SEQ ID NO:42) (oh-siRNA6), those obtained by annealing GGAAACCUACAACAACAUCtt (SEQ ID NO:43) and GAUGUUGUUGUAGGUUUCCtt (SEQ ID NO:44) (oh-siRNA7), and those obtained by annealing CAUCAACAUCAUCCAUGUCtt (SEQ ID NO:45) and GACAUGGAUGAUGUUGAUGtt (SEQ ID NO:46) (oh-siRNA8).

As one embodiment of the siRNA molecule of the present invention, the siRNA encompasses a short hairpin RNA (hereinafter, referred to as siRNA), in which the two RNA strands constituting the double-stranded RNA section are connected with a RNA section which is capable of forming a hairpin loop. In the shRNA, a sense RNA sequence and an antisense sequence constituting the double-stranded RNA section are connected with a RNA section which is capable of forming a hairpin loop, and the sense RNA sequence and the antisense sequence constitute a double-strand configuration. The chain length and the nucleotide sequence of the RNA section that forms a hairpin loop are not limited as long as the RNA section can form a hairpin loop, but the chain length is preferably 3 to 23, more preferably, 3 to 10, and examples of the RNA section include, for example, RNAs consisting of at least one nucleotide sequence selected from a group consisting of UUCAAGAGA, CUUCCUGUCA (SEQ ID No. 30), CCACC, CUCGAG, CCACACC, UUCAAGAGA, AUG, CCC, and UUCG. Examples of shRNAs containing a double-stranded RNA-forming section of the siRNA-6as and the siRNA-6s, a double-stranded RNA-forming section of the siRNA-7as and the siRNA-7s, and a double-stranded RNA-forming section of the siRNA-8as and the siRNA-8s (hereinafter, referred to as shRNA6, shRNA7, and shRNA8, respectively) are shown in Table 4.

TABLE 4

| Name | Base sequence |
|---|---|
| shRNA6 | UUUGAGAGACGAAGGAUACUUCAAGAGAGUAUCCUUCGUCUCUCAAA (SEQ ID No. 15) |
| shRNA7 | GGAAACCUACAACAACAUCUUCAAGAGAGAUGUUGUUGUAGGUUUCC (SEQ ID No. 20) |
| shRNA8 | CAUCAACAUCAUCCAUGUCUUCAAGAGAGACAUGGAUGAUGUUGAUG (SEQ ID No. 25) |

The siRNA molecule of the present invention can be manufactured by a known manufacturing method such as chemical synthesis or enzymatic synthesis, or can be manufactured with genetic engineering procedures by insertion into a suitable expression vector, as described below.

Examples of the chemical synthesis include a method of using a protective group such as 2'-ACE (2'-bis(acetoxymethoxy)-methylether) or 2'-TBDMS (2'-t-butyldimethylsillyl). Examples of the enzymatic synthesis include a method of using a RNA polymerase such as T7RNA polymerase. A double-stranded RNA synthesized by the chemical synthesis or the enzymatic synthesis may be modified by a chemical group for stabilization or labeling thereof.

The DNA of the present invention may be those introduced into a cell in a straight DNA form to produce siRNA in the cell. The DNA is not particularly limited, but examples of the DNA include DNA containing a DNA section that encodes the double-stranded oligonucleotide or the shRNA, a promoter capable of controlling transcription of the DNA section at the 5' end thereof, and a terminator at the 3' end thereof. Furthermore, such DNA can be inserted into a vector to prepare a vector of the present invention. Hereinafter, the DNA and the vector of the present invention will be illustrated by a preparation of the vector.

In a case of a DNA that can produce a double-stranded oligonucleotide, a sense strand and an antisense strand may each be disposed under control of a different promoter, whereby the sense strand and the antisense strand may be transcribed separately. When such DNA is inserted into a vector, examples of a vector include: (1) a tandem type vector in which each DNA is disposed in the forward direction, (2) an opposite type vector in which a DNA that encodes one RNA strand of the siRNA is disposed under a promoter that functions as a sense strand of the vector, and a DNA that encodes the other RNA strand of the siRNA is disposed under a promoter that functions as an antisense strand of the vector, and (3) separate type vectors in which a DNA that expresses a sense strand, and a DNA that expresses an antisense strand are inserted into separate vectors.

Furthermore, in the case of a DNA that can produce the above-mentioned shRNA, a DNA that can express the total length of shRNA may be used. For example, a DNA having a nucleotide sequence consisting of a sequence that encodes RNA of a sense strand downstream of a promoter, a sequence that encodes a hairpin loop, a sequence that encodes RNA of an antisense strand, a poly T stretch sequence, and a stop codon in order, may be used, and this DNA may be inserted into a vector.

The promoter is not particularly limited, but there may be mentioned a promoter for constitutive expression, or a promoter for expression under specific conditions. In particular, the promoter includes RNA polymerase III (pol III) promoter (Brummerlkamp, T. R., et al., Science, 297, 1352-1354, 2002), U6 promoter (Lee N S. et al., Nature Biotech. 20, 500-505, 2002; Miyagishi M. & Taira K., Nature Biotech. 20, 497-500, 2002; Paul C P. et al., Nature Biotech. 20, 505-508, 2002), H1 promoter (Brummelkamp T R et al: Science 296, 550-553, 2002), tRNA promoter (Oshima K., et al., Cancer Research 63, 6809-6814, 15, 2003), or the like.

The vector of the present invention is a vector for expression of siRNA that can suppress expression of mRNA of MUC5AC in a mammalian cell. Therefore, the basic vector is not particularly limited as long as it can express siRNA in good efficiency in the above cell. Examples of the basic vector include, for example, a plasmid vector and a straight double-stranded DNA vector, and virus vectors such as an adenovirus vector, an adeno-associated virus vector, a retrovirus vector and a lentivirus vector.

The siRNA, the DNA and the vector of the present invention can be introduced as siRNA, or as a pharmaceutical composition described below, into a tissue, or cell of interest, by means of microinjection method, electroporation method, particle gun method, or cation lipid method. When a virus vector is used as the basic vector, siRNA can be introduced by infection of the virus vector to a cell of interest.

The DNA or the vector of the present invention is transcribed into siRNA in a cell, and the resulting siRNA functions therein. Both transient and stable expressions can function effectively within a cell.

<<Action of the siRNA Molecule of the Present Invention>>

As shown in Examples described below, oh-siRNA1 to oh-siRNA8, which are the siRNAs of the present invention, suppressed expression of mRNA of MUC5AC specifically in a pancreatic cancer cell, SW1990. Furthermore, shRNA6, which is one embodiment of the siRNA molecule of the present invention, significantly suppressed mRNA expression of MUC5AC and protein expression of MUC5AC in a pancreatic cancer cell, SW1990 in which MUC5AC is expressed. The in-vitro proliferative ability of pancreatic cancer cells, SW1990 cell line, in which this shRNA6 is stably transcribed (hereinafter, sometimes referred to as the SW1990 si cell line), is the same as that of a pancreatic cancer cell, SW1990 cell line, to which a control vector is introduced (hereinafter, sometimes referred to as the SW1990 mock cell line). In other words, shRNA6, which is siRNA for MUC5AC, had no influence on proliferation of a pancreatic cancer cell itself. In addition, the SW1990 si cell line was also the same as the SW1990 mock cell line in adherence property, migration property, invasion performance, and the like.

However, the SW1990 si cell line was clearly different from the SW1990 mock cell line in proliferation property when it was subcutaneously injected to a nude mouse. That is, the SW1990 mock cell line increased rapidly in the tumor volume after the injection, whereas the SW1990 si cell line hardly increased in tumor volume. The proliferation of the SW1990 si cell line is suppressed. In other words, the siRNA for MUC5AC can suppress proliferation of pancreatic cancer cells in vivo.

The reasons why the siRNA molecule of the present invention can suppress proliferation of pancreatic cancer cells in vivo are considered to be as follows by analysis of the Examples described below. However, the present invention is not limited to those explained below.

Cancer cells usually cause immune reaction in a living body, and the immune reaction attempts to exclude the cancer cells from the body. However, in the living body with the SW1990 mock cell line that expresses MUC5AC, host immune function is suppressed by MUC5AC, and the cancer cells cannot be excluded. On the other hand, it is considered that, in the living body with the SW1990 si cell line, which does not express MUC5AC, host immune function is not suppressed, and thus cancer cell proliferation is suppressed.

Examples of specific immune suppression mechanism of MUC5AC include the following. In the living body with the SW1990 mock cell line in which MUC5AC is expressed, granulocytes barely exist on the surface and inside of a tumor, whereas in the living body with the SW1990 si cell line, invasion of leucocyte into the inside of a tumor was observed. These leucocytes are mainly B cell, granulocyte, and monocyte/macrophage and the like, and thus, it is understood that MUC5AC widely suppresses an activities of immune cells. Accordingly, the immune activity of neutrophil, which account for 90% or more of granulocytes, is also suppressed by MUC5AC.

Neutrophil has an important role as an immune cell, as described in details below, and the pharmaceutical composition of the present invention, particularly an immunosuppressive agent can suppress immune activity of neutrophil.

Neutrophil is mainly known as immune cells for bacteria by direct phagocytosis of bacteria or phagocytosis of encapsulated membrane bacteria after opsonization. However, it has been reported in recent years that neutrophil has an anti-tumor activity. It is known that the anti-tumor activity of neutrophil is caused by the induction of apoptosis via TNF related apoptosis inducing ligand (TRAIL). In 1995, TRAIL was isolated as a cytokine that can induce apoptosis and has a sequence similar to that of TNF family. As for the configuration of TRAIL, TRAIL is an about 30 kDa type II cell surface protein consisting of 281 amino acids, and has about 28% homology with Fas ligand. One great feature of TRAIL is that it shows can induce apoptosis in various malignant tumors, but has no cell toxicity for normal cells. Thus, it is one of the molecules that are expected to be applied as a molecular target drug. There are 5 kinds of receptor for TRAIL: TRAIL-R1 (Death Receptor 4: DR4), TRAIL-R2 (Death Receptor 5: DR5), TRAIL-R3 (Decoy Receptor 1: DcR1), TRAIL-R4 (Decoy Receptor 2: DcR2), and Osterprotegerin (OPG). DR4 and DR 5 have a death domain in cells, and are associated with induction of apoptosis, whereas DcR1 and DcR2 are Decoy receptors and do not induce apoptosis. Although there is a theory that induction of apoptosis by TRAIL only in malignant tumors is due to the difference of expression between these receptors, but the details thereof are unknown. Furthermore, it is known that TRAIL expression in neutrophil is significantly higher than that in other hematocytes.

In addition, the amount of PGE2 produced from macrophage was examined by co-culturing macrophage and the SW1990 mock cell line, or macrophage and the SW1990 si cell line. The amount of PGE2 obtained by co-culturing with the SW1990 si cell line was $1/7$ to $1/10$ compared to that obtained by co-culturing with the SW1990 mock cell line. In other words, MUC5AC enhances the production of PGE2 from macrophage, and causes immune suppression.

Furthermore, the specific antibody for pancreatic cancer cells was produced in a mouse injected with the SW1990 si cell line, whereas the specific antibody for pancreatic cancer cells was hardly produced in a mouse injected with the SW1990 mock cell line. That is, MUC5AC suppresses antibody production by B cells.

As described above, it is considered that suppression of MUC5AC expression by siRNA can induce (recover) host immune response suppressed by MUC5AC, whereby the in vivo proliferation of pancreas cancer cells are suppressed.

As described above, the present inventors have found that MUC5AC suppresses host immune function, whereby cancer cells escape from immune cells. As a result, an environment suitable for proliferation of cancer cells is created. In other words, the present inventors have found that immune suppression by MUC5AC is due to: (a) suppression of invasion of leucocytes (particularly neutrophil, B cell, and macrophage) into a cancer tissue, (b) suppression of antibody production of B cell, (c) suppression of cytotoxic activity of mononuclear cells and polynuclear cells, (d) suppression of mitogen activity, (e) promotion of prostaglandin E2 production, and (f) suppression of apoptosis via TRAIL, and the like, and has effects for a wide range of immune cells.

Accordingly, the present specification discloses a pharmaceutical composition comprising mucin subtype 5 AC as an active ingredient.

The present specification also discloses an immunosuppressive agent comprising mucin subtype 5 AC as an active ingredient.

According to a preferable embodiment of the immunosuppressive agent, it suppresses function of leucocyte.

According to a preferable embodiment of the immunosuppressive agent, it suppresses mitogenic activity.

According to a preferable embodiment of the immunosuppressive agent, it promotes prostaglandin production.

According to a preferable embodiment of the immunosuppressive agent, it suppresses antibody production of B cell.

According to a preferable embodiment of the immunosuppressive agent, it suppresses apoptosis.

The immunosuppressive agent allows: (1) prevention and treatment of rejection reaction for a transplanted organ in organ transplant, (2) prevention and treatment of autoimmune disease, and (3) prevention and treatment of allergic asthma. The above pharmaceutical composition, specifically an immunosuppressive agent, has suppressive effects for a wide range of immune cells, and thus has effects for various diseases that are improved by immune suppression. Furthermore, MUC5AC, which is an active ingredient of the immunosuppressive agent, is a glycoprotein originally existing in vivo, and thus is found to have no adverse effects such as renal disorder, arteriolar disorder, hypertension, diabetes, and hyperlipidemia, which are problems of conventional immunosuppressive agents, for example, cyclosporine A.

The above-mentioned pharmaceutical composition, specifically an immunosuppressive agent, can suppress functions of a wide range of immune cells, and thus is useful in treating or preventing diseases that are considered to be immune-related including, for example, autoimmune diseases. Examples of immune-related diseases include systemic lupus erythematosus, inflammatory bowel disease (for example, ulcerative colitis, Crohn's disease), multiple sclerosis, psoriasis, chronic hepatitis, bladder carcinoma, breast cancer, cancer of the uterine cervix, chronic lymphocytic leukemia, chronic mylogenous leukemia, carcinoma of the colon, colonic cancer, rectal cancer, Helicobacter Pylori bacterial infectious disease, Hodgkin's disease, insulin dependent diabetes mellitus, malignant melanoma, multiple myeloma, non-Hodgikin's lymphoma, non-small cell lung cancer, ovarian cancer, peptic ulcer, prostatic cancer, septic shock, tuberculosis, sterility, arteriosclerosis, Behcet's disease, asthma, atopic dermatitis, nephritis, systemic fungal infection, acute bacterial meningitis, acute myocardial infarction, acute pancreatitis, acute viral encephalitis, adult respiratory distress syndrome, bacterial pneumonia, chronic pancreatitis, herpes simplex virus infection, varicellazoster viral infectious disease, AIDS, human papilloma viral infectious disease, influenza, invasive staphylococcal infectious disease, peripheral vessel disease, sepsis, interstitial hepatic disease, regional ileitis, and multiple sclerosis.

2. Drug Screening Using siRNA-Introduced Cell

Using the knocked down cell of the present invention and a MUC5AC expression cell (for example, a mother cell line of the knocked down cell line), it is possible to screen whether or not a test substance modifies (for example, suppresses or promotes) proliferation, invasion performance, chemotaxis, adherence property, morphology, or the like of a cell expressing MUC5AC. In other words, it is possible to screen whether or not a test substance binds to native MUC5AC by bringing a MUC5AC expression cell and a knocked down cell into contact with the test substance.

Furthermore, by comparing reaction of a MUC5AC expression cell with that of a knocked down cell, it is possible to screen whether or not a test substance binds to native MUC5AC, and has influence on proliferation, invasion performance, chemotaxis, adherence property, morphology or the like of a MUC5AC expression cell line.

The test substance that may be applied to the screening method of the present invention is not particularly limited, but examples of the test substance include various known compounds (including peptides) registered in chemical files, compounds obtained by the combinatorial chemistry techniques [Terrett, N. K. et al., Tetrahedron, 51, 8135-8137 (1995)] or usual synthesis techniques, or a group of random peptides prepared by employing a phage display method [Felici, F. et al., J. Mol. Biol., 222, 301-310 (1991)], or the like. In addition, culture supernatants of microorganisms, natural components derived from plants or marine organisms, or animal tissue extracts and the like may be also used as the test substance for screening. Furthermore, compounds (including peptides) obtained by chemically or biologically modifying compounds (including peptides) selected by the screening method of the present invention may be used.

First, MUC5AC expression cell line and knocked down cell line may be used in screening of binding of a test substance to native MUC5AC. Evaluation whether or not a test substance binds to a native structure antigen, is generally conducted by using cells which excessively express a target antigen and cells that do not express a target antigen. However, in a case of ultra-high molecular glycoprotein such as MUC5AC, it is not easy to highly express the full-length protein in cells. Accordingly, it is preferable to investigate binding of a test substance to native MUC5AC, by means of MUC5AC knock-down cell obtained by introduction of siRNA into MUC5AC-high expression cell.

Furthermore, in the screening method of the present invention, the MUC5AC expression cell line and the knocked down cell line are brought into contact with a test substance, whereby any influence on proliferation of the MUC5AC expression cell line in the presence of the test substance can be analyzed. As a result, it can be determined whether or not the test substance modifies proliferation, invasion performance, chemotaxis, adherence property, morphology, or the like, of the MUC5AC expression cell line. For example, when the growth of the MUC5AC expression cell line decreases in the presence of the test substance compared to the proliferation of the MUC5AC expression cell line in the absence of the test substance, it is judged that such test substance suppresses or inhibits proliferation of the MUC5AC expression cell line. On the other hand, when the growth of the MUC5AC expression cell line increases, it is judged that such a test substance promotes proliferation of the MUC5AC expression cell line. Such influence of the test substance on proliferation of the MUC5AC expression cell line is not seen for the knocked down cell line in which MUC5AC expression is suppressed, and thus the knocked down cell line can be used as a negative control.

3. Pharmaceutical Composition of the Present Invention

The pharmaceutical composition of the present invention may comprise the siRNA, DNA, or vector of the present invention.

The siRNA of the present invention, or DNA or vector capable of transcribing the above siRNA in a subject can be administered, in an effective amount, alone, or preferably together with a pharmaceutically or veterinarily acceptable carrier or diluent, to a subject (for example, an animal, preferably a mammal, particularly a human) in need of a prevention and/or treatment of a disease involving an overexpression of mucin subtype 5 AC and an cell proliferation. For example, the siRNA of the present invention, or DNA or vector capable of transcribing the above siRNA in a subject to be administered, can be used to treat a cancer, in particular pancreatic cancer by being administered alone, or preferably together with a pharmaceutically or veterinarily acceptable carrier or diluent, and by inhibiting proliferation of MUC5AC expressing cells in vivo. In addition, the siRNA DNA, or vector of the present invention can improve symptoms of asthma by inhibiting the expression of MUC5AC in cells or suppressing a secretion of MUC5AC.

The disease, which is treated by the pharmaceutical composition of the present invention, is a disease involving an overexpression of mucin subtype 5 AC, in particular, cancer and asthma may be mentioned. The above cancer includes, but is not particularly limited to, for example, bladder cancer, breast cancer, colon cancer, kidney cancer, hepatic cancer, lung cancer, small cell lung cancer, esophageal cancer, gallbladder cancer, ovarian cancer, pancreatic cancer, stomach cancer, cervical cancer, thyroid cancer, prostate cancer, squamous cancer, skin cancer, osteocarcinoma, lymphoma, leukemia, and brain cancer. According to the pharmaceutical composition of the present invention, pancreatic cancer, lung cancer, breast cancer, stomach cancer, cervical cancer, and colon cancer can be treated effectively.

The formulation of the pharmaceutical composition of the present invention is not limited. However, there may be mentioned oral agents, such as powders, subtle granules, granules, tablets, capsules, suspensions, emulsions, sylups, extracts, or balls; or parentarnal agents, such as injections, liquid for external use, ointments, suppositorys, creams for local administration, or eye-drops.

The above oral agent can be prepared in accordance with conventional methods, using fillers, such as gelatin, alginate sodium, starch, cornstarch, saccharose, lactose, glucose, mannitol, carboxymethyl-cellulose, dextrin, polyvinyl pyrrolidone, clystalline cellulose, soy lecithin, sucrose, fatty acid ester, talc, magnesium stearate, polyethylene glycol, magnesium silicate, silicic anhydride, or synthetic aluminum silicate; binders, disintegrators, detergents, lubricants, flow accelerator, diluents, preservatives, colorants, flavors, correctives, stabilizers, humectants, antiseptics, antioxidant, or the like Examples of the parentarnal administration include injection (for example, subcutaneous injection or intravenous injection), rectal administration, or the like. Among them, the injections are preferably used.

For example, in a preparation of the injections, an aqueous solvent such as normal saline solution or Ringer solution, non-aqueous solutions such as plant oil or fatty acid ester, a tonicity agent such as glucose or sodium chloride, a solubility assisting agent, a stabilizing agent, an antiseptic agent, a suspending agent, or an emulsifying agent, may be optionally used, in addition to the active ingredient.

Further, the pharmaceutical composition of the present invention may be administered by means of sustained-release formulation using sustained-release polymer. For example, the pharmaceutical composition of the present invention is introduced into a pellet of ethylene vinyl acetate polymer, and then the pellet can be surgically implanted into a tissue to be treated or prevented.

The pharmaceutical composition may contain, but is not limited to, 0.01 to 99% by weight, preferably 0.1 to 80% by weight, of the active ingredient.

A dose of the pharmaceutical composition of the present invention may be appropriately determined in accordance with, for example, age, sex, body weight, or degree of symptom of each patient, the type of each active ingredient, type of each disease, route of administration, or the like, and the determined dosage can be administered orally or parenterally.

In addition, dosage form for administration of the pharmaceutical composition of the present invention is not limited to a drug medicine. That is, it can be administered as a food and drink of various form, such as a functional food, a healthy food (including drink), or an animal food stuff.

EXAMPLES

The present invention will now be further illustrated by, but is by no means limited to, the following Examples.

EXAMPLES

Example 1

Suppression of MUC5AC Expression by Overhang Double-Stranded siRNA

An overhang double-stranded siRNA in which tt was added to the 3' end of 19 mer RNA was introduced to a pancreatic cancer cell line, SW1990 in which MUC5AC is expressed, and suppression of MUC5AC expression was investigated. Eight sequences of the overhang double-stranded siRNAs corresponding to the target mRNA regions 1 to 8 are shown in Table 5.

TABLE 5

| Name | Sequence |
|---|---|
| oh-siRNA1 | G G A G C C U G A U C A U C C A G C A t t (SEQ ID NO: 31) |
| | t t C C U C G G A C U A G U A G G U C G U (SEQ ID NO: 32) |
| oh-siRNA2 | G C A G G C A C U U C U C C A G G A t t (SEQ ID NO: 33) |
| | t t C G U C C G U G A A G A G G G U C C U (SEQ ID NO: 34) |
| oh-siRNA3 | G C A G U G C C U U C A C U G U A C U t t (SEQ ID NO: 35) |
| | t t C G U C A C G G A A G U G A C A U G A (SEQ ID NO: 36) |
| oh-siRNA4 | A C A C C A A G C U G A C A C C C A U t t (SEQ ID NO: 37) |
| | t t U G U G G U U C G A C U G U G G G U A (SEQ ID NO: 38) |
| oh-siRNA5 | C C C U C A A C C U U C U U C A U C A t t (SEQ ID NO: 39) |
| | t t G G G A G U U G G A A G A A G U A G U (SEQ ID NO: 40) |
| oh-siRNA6 | U U U G A G A G A C G A A G G A U A C t t (SEQ ID NO: 41) |
| | t t A A A C U C U C U G C U U C C U A U G (SEQ ID NO: 42) |
| oh-siRNA7 | G G A A A C C U A C A A C A A C A U C t t (SEQ ID NO: 43) |
| | t t C C U U U G G A U G U U G U U G U A G (SEQ ID NO: 44) |
| oh-siRNA8 | C A U C A A C A U C A U C C A U G U C t t (SEQ ID NO: 45) |
| | t t G U A G U U G U A G U A G G U A C A G (SEQ ID NO: 46) |

Each of the single-stranded RNAs of oh-siRNA1 to oh-siRNA8 shown in Table 5 was synthesized according to a usual method. To the synthesized sense RNA and the antisense RNA, an annealing buffer was added, and the mixture was treated at 95° C. for 1 minute, and then kept at 37° C. for 1 hour, and subject to annealing, which was used in transfection to the SW1990 cell line.

$2 \times 10^5$ cells/well of the SW1990 cell line were seeded in on a 6 well plate, and cultured to 50 to 90% confluency. To 250 µL of a serum-free DMEM medium, siRNA was added to give 1 µM of final concentration (Solution A). To another 250 µL of a serum-free DMEM medium, 5 µL of Lipofectamin 2000 (manufactured by Invitrogen) was added and the whole was incubated at room temperature for 5 minutes (Solution B). Solution A and solution B were mixed, and the mixture was incubated at room temperature for a further 20 minutes, and then a DMEM medium containing 2 mL serum was added, and 2.5 mL of the total amount was added to the cells. The cells were cultured for 48 hours, and then collected.

MUC5AC expression in the SW1990 cell line to which oh-siRNA1 to oh-siRNA8 had been introduced, was investigated by RT-PCR. From the collected SW1990 cell line, total RNA was extracted using RNeasy Mini Kit (manufactured by QIAGEN), and purified. RT-PCR was performed using a sense primer 5'-GCCACCGCTGCGGCCTTCTTC-3'(SEQ ID No. 26) and an antisense primer 5'-GTGCACGTAGGAGGACAGCGC-3'(SEQ ID No. 27), which are specific to the nucleotide sequence of MUC5AC according to the user instruction attached to the SuperScript III First Strand Synthesis System (manufactured by Invitrogen). By this approach transcription of MUC5AC mRNA was investigated. As a control, a sense primer 5'-TCCTGCACCACCAACTGCTTAG-3'(SEQ ID No. 28) and an antisense primer 5'-TCTTACTCCTTGGAGGCCATGT-3'(SEQ ID No. 29), which are specific to the nucleotide sequence of GAPDH, were used, and mRNA of GAPDH was measured.

As shown in FIG. 1, suppression of mRNA expression of MUC5AC was observed in the SW1990 cell line transfected with siRNA in comparison to the SW1990 cell line that was not transfected with siRNA. Particularly, oh-siRNA1 and oh-siRNA6 showed strong mRNA suppression.

Example 2

Construction of Plasmid Vector that Encodes shRNA6, shRNA7, and shRNA8

(A) In order to construct a vector that transcribes shRNA6, shRNA7, and shRNA8, which correspond to the above-mentioned target mRNA regions 6, 7, and 8 respectively, DNAs of shDNA6-1 (SEQ ID No. 13) and shDNA6-2 (SEQ ID No. 14), shDNA7-1 (SEQ ID No. 18) and shDNA7-2 (SEQ ID No. 19), and shDNA8-1 (SEQ ID No. 23) and shDNA8-2 (SEQ ID No. 24) were synthesized by an ordinary method.

Sense strand of shRNA6:
(SEQ ID No. 13)
GATCCGTTTGAGAGACGAAGGATACTTCAAGAGAGTATCCTTCGTCTCTC

AAATTTTTTGGAAA,

-continued

```
Antisense strand of shRNA6:
                                      (SEQ ID No. 14)
AGCTTTTCCAAAAAATTTGAGAGACGAAGGATACTCTCTTGAAGTATCCT

TCGTCTCTCAAACG,

Sense strand of shRNA7:
                                      (SEQ ID No. 18)
GATCCGGAAACCTACAACAACATCTTCAAGAGAGATGTTGTTGTAGGTTT

CCTTTTTTGGAAA,

Antisense strand of shRNA7:
                                      (SEQ ID No. 19)
AGCTTTTCCAAAAAAGGAAACCTACAACAACATCTCTCTTGAAGATGTTG

TTGTAGGTTTCCG,

Sense strand of shRNA8:
                                      (SEQ ID No. 23)
GATCCGCATCAACATCATCCATGTCTTCAAGAGAGACATGGATGATGTTG

ATGTTTTTTGGAAA,

Antisense strand of shRNA8:
                                      (SEQ ID No. 24)
AGCTTTTCCAAAAAACATCAACATCATCCATGTCTCTCTTGAAGACATGG

ATGATGTTGATGCG
``` shDNA6-1 (SEQ ID No. 13) contains DNA that encodes RNA consisting of a nucleotide sequence that is homologous to certain part of the nucleotide sequence of human MUC5AC mRNA (sense strand), DNA that encodes RNA complementary to the above nucleotide sequence (antisense strand), and DNA that encodes RNA of a loop section therebetween. Furthermore, shDNA6-1 contains DNA that encodes RNA polymerase III terminator at 3' end of the DNA consisting of the sense strand, the loop section and the antisense strand, and one nucleotide "g" at the 5' end of the sense strand to increase transcription efficiency. In addition, for insertion into the vector pSilencer 3.1 neo (manufactured by Ambion Inc.), there are BamH I site at the 5' end and Hind III site at the 3' end. The nucleotide sequence of shDNA6-2 (SEQ ID No. 14) is complementary to the nucleotide sequence of shDNA6-1 (SEQ ID No. 13) except the restriction enzyme sites. That is, and shDNA6-2 has BamH I site at the 5' end and Hind III site at the 3' end. Specifically, shDNA6-1 and shDNA6-2 were subject to annealing, and digested with BamH I and Hind III, and then ligated to the cleaved sites of pSilencer 3.1 neovector digested with the above restriction enzymes, to give a vector containing DNA that encodes shRNA6 (hereinafter, referred to as the shRNA6 vector).

Similar procedures were repeated except that shDNA7-1 and shDNA7-2, or shDNA8-1 and shDNA8-2 were used instead of shDNA6-1 and shDNA6-2, to give shRNA7 vector, and shRNA8 vector.

Example 3

Preparation of MUC5AC Knock-Down Cell Line by Introduction of shRNA6 Vector into Pancreatic Cancer Cell Line, SW1990

(A) The pancreatic-cancer cell line, SW1990 was transfected with shRNA6 vector corresponding to oh-siRNA6, which had good efficiency in transient expression in the SW1990 cell line, among the three vectors prepared in Example 2.

The pancreatic-cancer cell line, SW1990 was cultured in RPMI1640 containing 10% fetal bovine serum (added with 100 U/mL penicillin and 100 μg/mL streptomycin; hereinafter, referred to as complete RPMI1640 medium) under the environment of 37° C. and 5% $CO_2$, and maintained. $1 \times 10^6$ of each cell were seeded in a cell culture dish of 10 cm diameter, and after 24 hours, the cells became 70 to 90% confluent. 11.2 μg of the shRNA6 vector was dissolved in 56 μL of Lipofectamine 2000 (manufactured by Invitrogen), and added to the dish with the cells, and cultured at 37° C. After 24 hours, the medium was substituted with a medium in which GENETICIN (G418, manufactured by GIBCO) was added to give a final concentration of 400 μg/mL to the above-mentioned complete RPMI1640 medium.

(B) Selection with the above-mentioned G418 gave SW1990 si cell line in which shRNA6 was stably transcribed. Similar procedures were repeated except that pSilencer 3.1 neo was used instead of the shRNA6 vector, to give a SW1990 mock cell line as a control.

Example 4 mRNA Transcription of MUC5AC and Expression of MUC5AC in the SW1990 si Cell Line mRNA transcription of MUC5AC in the SW1990 si cell line was examined by RT-PCR.

The procedures of RT-PCR in Example 1 were repeated except that total RNA derived from the SW1990 si cell line was extracted and purified using RNeasy Mini Kit (manufactured by QIAGEN). By this method mRNAs of MUC5AC and GAPDH were measured.

Figure 2:
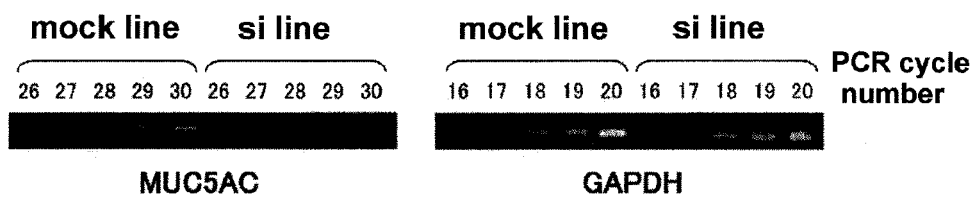
FIG. 2 is a photograph of electrophoresis showing the genetic expression of MUC5AC in SW1990 si cell line or SW1990 mock cell line. The expression of GAPDH in SW1990 cells transfected with siRNA of GAPDH and mock transfected SW1990 cells, were examined as controls.

As shown in FIG. 2, it was found that expression was significantly suppressed in the SW1990 si cell line compared to the SW1990 mock cell line.

The expression MUC5AC protein was evaluated by Fluorescence Activated Cell Sorting (FACS). To each cell adjusted to $10^6$ cells/50 μL, 1 μg of anti-MUC5AC antibody (M5#1) was added, and the cell was incubated on ice for 30 minutes. Non-bound antibodies were washed, and then anti-mouse IgG-FITC was added to the cell, and incubated further on ice for 30 minutes. Non-bound antibodies were washed, and then analysis by FACS was performed.

Figure 3:
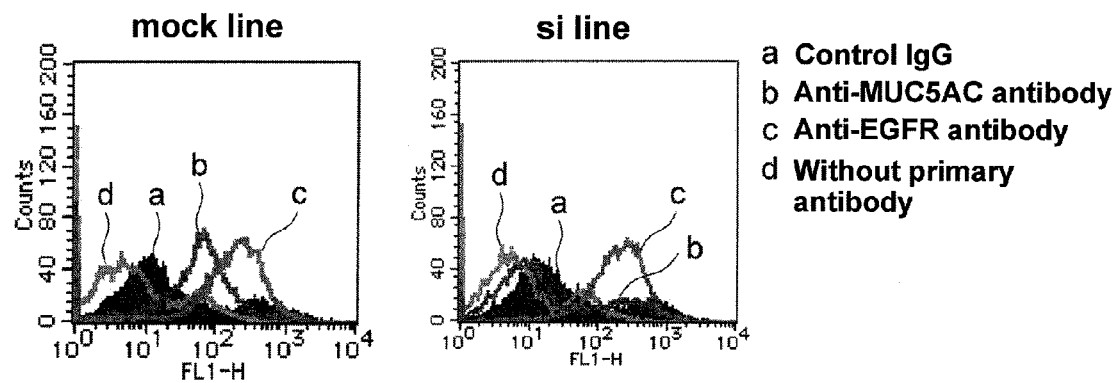
FIG. 3 is a graph analyzing by FACS the expression of MUC5AC protein in SW1990 si cell line or SW1990 mock cell line.

As shown in FIG. 3, a shift (showing that the antibody was bound to the cell) was found in the SW1990 mock cell line, but was not found in the SW1990 si cell line. Accordingly, from these results, it was found that MUC5AC was knocked down in the gene and the protein, and the expression of MUC5AC disappeared by the action of siRNA in the SW1990 si cell line.

Example 5

Investigation of Cell Proliferation by siRNA In Vitro

In this Example 5, the proliferative ability of the SW1990 si cell line and the SW1990 mock cell line in vitro were investigated by MTT assay.

$10^3$ cells/well of the SW1990 si cell line and the SW1990 mock cell line were seeded on a 96 well plate, and with MTT reagent (manufactured by DOJINDO) was added and incubated for 3 hours. The medium was removed, and then 100 μL of DMSO was added, and absorbance at 570 to 630 nm was measured. MTT agent was again added, incubated and removed, and the measurement repeated on the 1st, 2nd, 3rd, 4th and 7th day.

Figure 4:
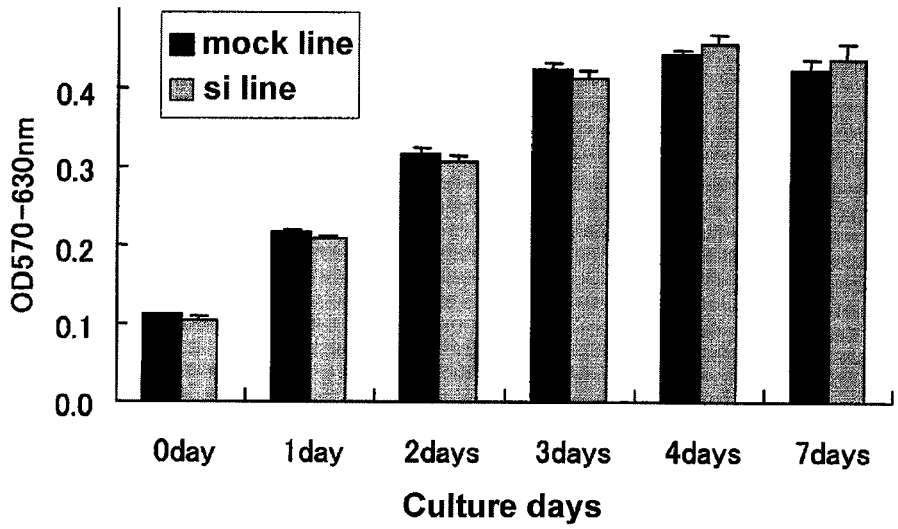
FIG. 4 is a graph showing the in vivo proliferation of SW1990 si cell line (MUC5AC knock-down cell line) or SW1990 mock cell line.

As shown in FIG. 4, both of the SW1990 si cell line and the SW1990 mock cell line proliferated at similar speed on the 1st, 2nd, and 3rd days, and became confluent on 4th day or later, and cell proliferation stopped in both cell lines. The speed of cell proliferation was not found to be different between the SW1990 si cell line and the SW1990 mock cell line in vitro.

Accordingly, suppression of MUC5AC transcription by siRNA had no influence on proliferation of the cancer cells in vitro.

Example 6

Investigation of Cell Proliferation by siRNA In Vivo

In this Example 6, proliferative abilities of the SW1990 si cell line and the SW1990 mock cell line in vivo were investigated by injection thereof to a nude mouse.

$10^7$ cells/mouse of the SW1990 si cell line and the SW1990 mock cell line were subcutaneously injected in to a nude mouse (n=10), and then the tumor radius and the body weight were measured and evaluated according to time course. The tumor volume was calculated using the equation below.

$$\text{Tumor volume} = \text{long radius} \times (\text{short radius})^2 \times 0.5236 \quad \text{<<Equation 1>>}$$

Figure 5:
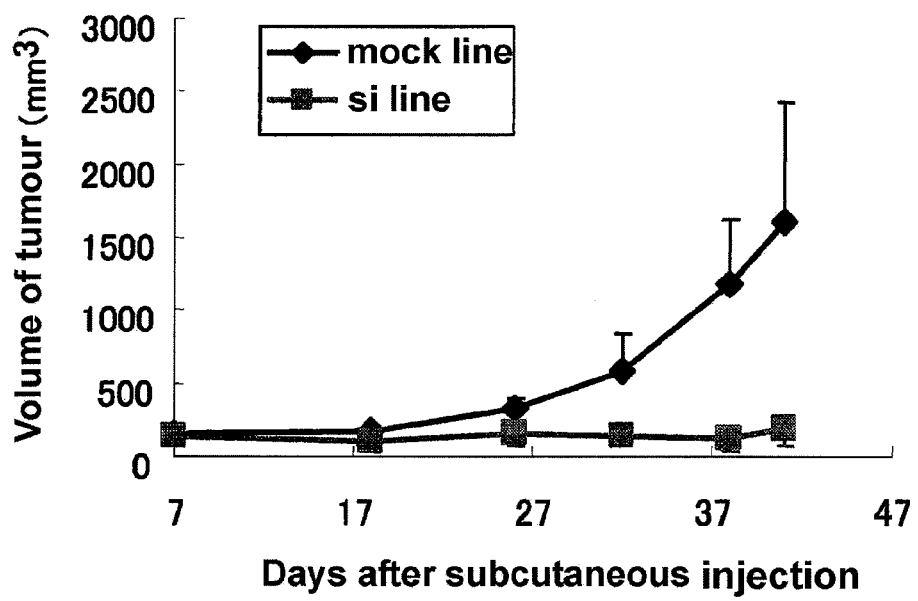
FIG. 5 is a graph showing the in vivo proliferation of the SW1990 si cell line (MUC5AC knock-down cell line) or the SW1990 mock cell line injected subcutaneously into a nude mouse.

The tumor volume in the SW1990 mock cell line was 157, 163, 316, 575, 1177 and 1598 mm$^3$, on the 7th, 18th, 26th, 32th, 38th and 41th day after the injection, respectively, and increased on 26th or later with time (FIG. 5). On the other hand, the tumor volume in the SW1990 si cell line was 137, 109, 159, 143, 120 and 181 mm$^3$, respectively, and found to hardly increase (FIG. 5).

Next, $10^6$ cells/mouse of the SW1990 mock cell line or the SW1990 si cell line was administered to the tail vein of a nude mouse, and lung metastasis was investigated. The mice were raised for 3 months after administration of the SW1990 si cell line and the SW1990 mock cell line, and then autopsy was performed. Metastasis number on the surface of the lung tissue was visually evaluated. In a group injected with the SW1990 mock cell line, lung metastasis was found for most of the subjects although the metastasis number varied. However, in a group injected with the SW1990 si cell line, the metastasis was not found for any subject (Table 6).

TABLE 6

| mock line injected group | | si line injected group | |
|---|---|---|---|
| Mouse No. | Metastasis number | Mouse No. | Metastasis number |
| 1 | 1 | 1 | 0 |
| 2 | 10 | 2 | 0 |
| 3 | 0 | 3 | 0 |
| 4 | dead | 4 | 0 |
| 5 | dead | 5 | 0 |
| 6 | 2 | 6 | 0 |
| 7 | 1 | 7 | 0 |
| 8 | 7 | 8 | 0 |
| 9 | 6 | 9 | 0 |
| 10 | 10 | 10 | 0 |
| 11 | 4 | 11 | 0 | siRNA cannot suppress cell proliferation of pancreatic cancer cell directly, but suppresses proliferation of pancreatic cancer cells in vivo. In addition, from the fact that metastasis of pancreatic cancer cells in the lungs was not found by intravenous administration, it can be seen that the siRNA molecule of the present invention can suppress proliferation of pancreatic cancer, and can suppress metastasis.

Example 7

Induction (Recovery) of Leucocyte Function by siRNA

In this Example 7, induction of immune function by siRNA for a pancreas cancer cell, SW1990 was examined by HE staining and immune staining.

Figure 6:
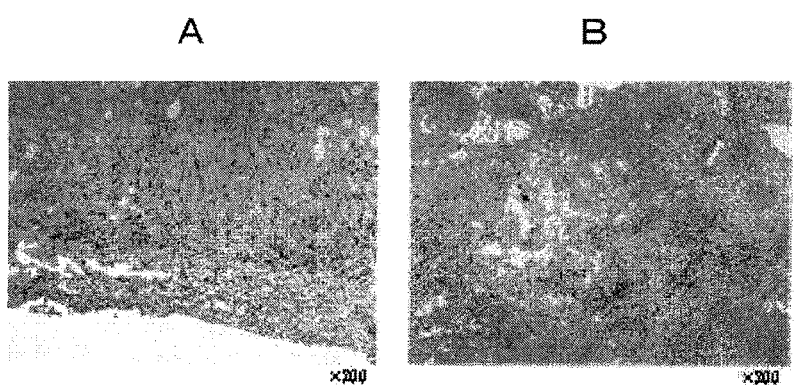
FIG. 6 is a photograph showing, using HE stain, an invasion of leucocyte into the tumor tissue in nude mice in which SW1990 si cell line (MUC5AC knock-down cell line) or SW1990 mock cell line had been injected subcutaneously. The SW1990 mock cell line is shown in (A), and the SW1990 si cell line is shown in (B).

A tumor tissue fragment of a mouse on 41th day of subcutaneous injection, to which the SW1990 si cell line and the SW1990 mock cell line were administered, was fixed with a neutral formalin solution, and a slide of tissue section was prepared according to an usual method. For the obtained tissue section, HE staining was performed. As shown in FIG. 6, with the mock cell line-transplanted group, a scattering of leucocyte (red globular form) was found near subcutaneous site, but no accumulation of leucocytes inside of the tumor was found. On the other hand, with the si cell line-transplanted group, the accumulation of leucocytes inside of the tumor was largely observed, in addition to the scattering of leucocyte near the subcutaneous site.

Figure 7:
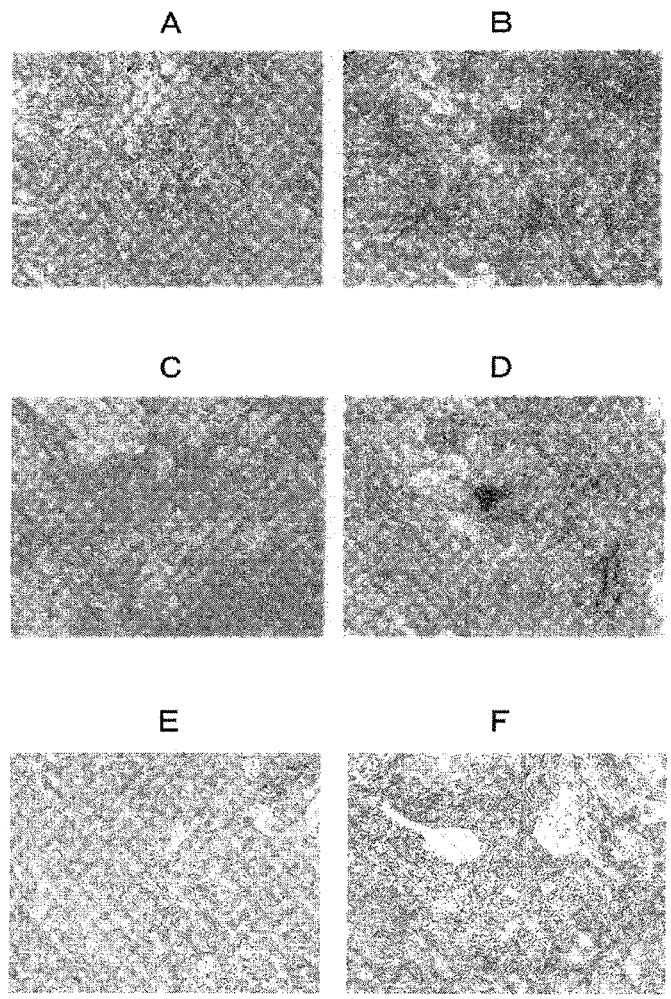
FIG. 7 is a photograph showing, using immunostaining, invasions of B cell, granulocyte, and macrophage into the tumor tissue in nude mice in which SW1990 si cell line (MUC5AC knock-down cell line) or SW1990 mock cell line is injected subcutaneously. The invasion of neutrophil in SW1990 mock cell line (A), the invasion of neutrophil in SW1990 si cell line (B), the invasion of B cell in SW1990 mock cell line (C), the invasion of B cell in SW1990 si cell line (D), the invasion of macrophage in SW1990 mock cell line (E), and the invasion of macrophage in SW1990 si cell line (F) are shown.

The leucocyte accumulated in the tumor was analyzed by immune staining of the above tissue-section slide. As primary antibodies for granulocyte and B cell, 1 μg/mL of rat anti-mouse Gr-1 antibody, rat anti-mouse CD45R/B220 antibody, and rat anti-mouse F4-80 antibody were used respectively. As a secondary antibody, anti-rat IgG-HRP (0.1 μg/mL) was used, and coloring was performed using DAB (manufactured by DAKO Japan) as a substrate. Then, nucleic staining by hematoxylin was performed. For the tumor tissue of the SW1990 si cell line, many accumulations of granulocyte, B cell and macrophage were observed (FIG. 7). On the other hand, for the tumor tissue of the SW1990 mock cell line, slight immune cell accumulation was observed, but the number of the accumulations was remarkably less in comparison to that of the si cell line transplant tumor (FIG. 7).

Accordingly, it was found that siRNA induces immune functions of leucocyte, particularly B cell, granulocyte, and macrophage for pancreatic cancer, SW1990.

Example 8

Production of Specific Antibody for a Pancreas Cancer Cell, SW1990 by siRNA

The suppressive effect of MUC5AC for antibody production was investigated. Blood was collected from a mouse injected with the SW1990 mock cell line or the SW1990 si cell line, and then the total IgG concentration was measured by the ELISA method, and the concentration thereof was adjusted for use in FACS. The antibody obtained by mixing of the antibodies for all mice (n=10) is used. FACS was conducted in the same method of FACS described in Example 2 using 1 μg of the antibody per $10^6$ PK45P cells (MUC5AC negative pancreatic cancer cell line).

Figure 8:
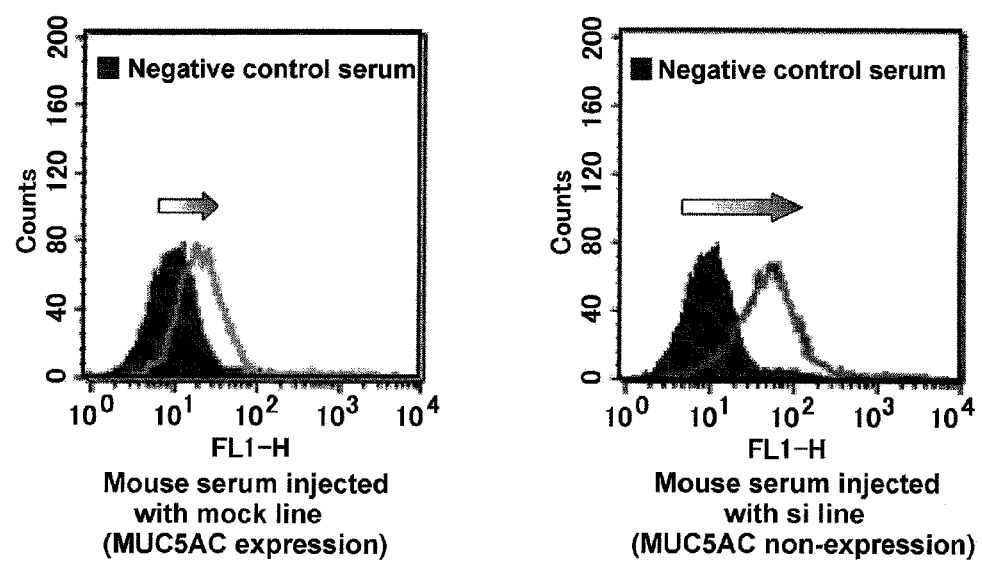
FIG. 8 is a graph of FACS analysis showing the antibody production by B cell in a nude mouse in which SW1990 si cell line (MUC5AC knock-down cell line) or SW1990 mock cell line had been injected subcutaneously.

As shown in FIG. 8, compared to the antibody of the group injected with the SW1990 mock cell line, cells stained by the antibody of the group injected the SW1990 si cell line were increased. That is the peak of stained cells was shifted to the right. In other words, the SW1990 si cell line-injected group produced high-potency antibody for the human cells, but antibody production is suppressed in the mice injected with the SW1990 mock cell line. The production of antibody for pancreatic cancer cells by siRNA was observed.

Example 9

In this Example 9, it was investigated whether or not immunity for SW1990 induced in the SW1990 si cell line-injected mouse is also effective for the SW1990 mock cell line. Specifically, the mouse that was immune-induced by injection of the SW1990 si cell line, was further injected with the SW1990 mock cell line.

Figure 9:
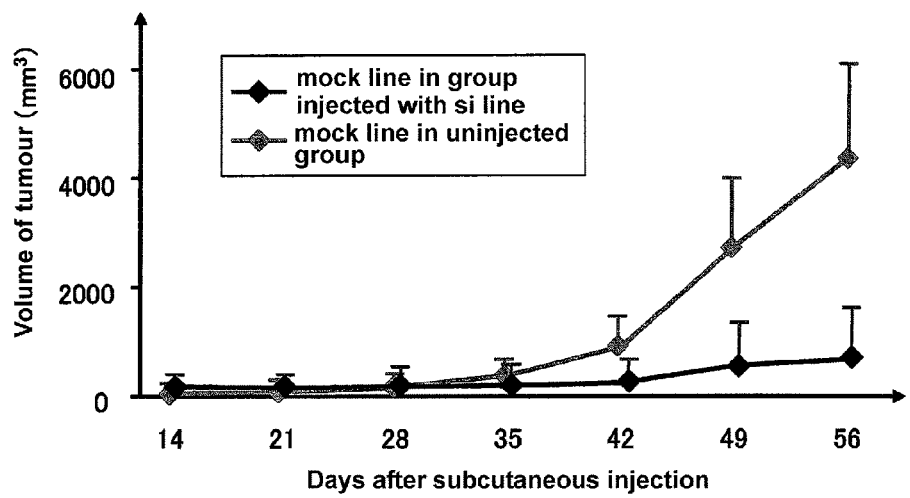
FIG. 9 is a graph showing the in vivo proliferation of SW1990 mock cell line injected into a nude mouse which had previously been injected with SW1990 si cell line.

The SW1990 si cell line was injected subcutaneously (right side), and after 35 days, the SW1990 mock cell line was subcutaneously injected to the other end (left side) with $1\times10^7$ cells/mouse, and formation of the tumor was observed. As shown in FIG. 9, the tumor volume of the SW1990 mock cell line in no-treatment group (control group), was 54, 82, 137, 300, 707, 2131 and 3368 $mm^3$, respectively on the 14th, 21st, 28th, 35th, 42nd, 49th and $56^{th}$ day after the injection. On the other hand, the tumor volume of the SW1990 mock cell line in the SW1990 si cell line-injected group remained at 17, 11, 17, 45, 110, 475 and 619 $mm^3$, respectively. That is, it is considered that the SW1990 si cell line that was first injected, induced immunity of the mouse, and the immunity suppressed proliferation of the SW1990 mock cell line.

Example 10

Prevention of Immune Suppression by siRNA

Influence of MUC5AC on PGE2 production from macrophage was investigated, as one mechanism for immune suppression in a mouse injected with pancreatic cancer cells being prevented by knock-down of MUC5AC expression by siRNA.

Figure 10:
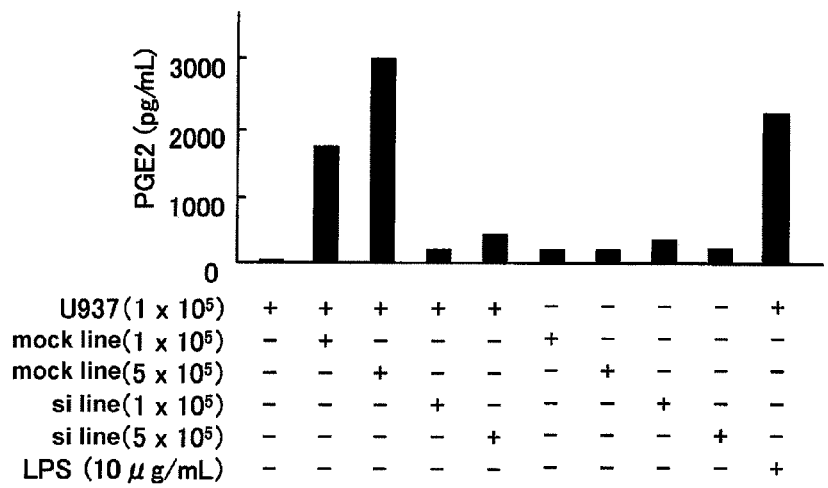
FIG. 10 is a graph showing the production of PGE2 by a stimulus of SW1990 mock cell line in which MUC5AC is expressed.

Human monocyte-based precursor cell, U937 cell line, was seeded at $10^5$ cells/well on a 12-well plate, and then differentiated to macrophage under presence of 50nM phorbol myristate acetate (PMA). After 48 hours, the medium was changed to a PMA-free medium, and incubated for a further 24 hours. Then, the SW1990 mock cell line or the SW1990 si cell line was seeded at $10^5$ and $5\times10^5$ cells/well, respectively in each of the wells, and co-cultured for 24 hours. The amount of PGE2 in the culture supernatant was then measured with a PGE2 EIA kit (manufactured by Cayman Chemical). The results are shown in FIG. 10.

In the group seeded with the U937 cell line alone, PGE2 production was 36 pg/mL, i.e., PGE2 was hardly produced. However, in a group of the U937 cell line co-cultured with the SW1990 mock cell line, PGE2 production increased with strong cell-number dependence: which was 1670 pg/mL in $1\times10^5$ cells, and 2965 pg/mL in $5\times10^5$ cells. On the other hand, in a group of the U937 cell line co-cultured with the SW1990 si cell line, PGE2 production was 167 pg/mL in $1\times10^5$ cells, and 408 pg/mL in $5\times10^5$ cells, i.e., the production amount was very low. In addition, in a group of the mock cell line alone, PGE2 production was 190 pg/mL and 319 pg/mL, with $1\times10^5$ cells and $5\times10^5$ cells, respectively, and in a group of the SW1990 si cell line alone, was 190 pg/mL and 214 pg/mL, with $1\times10^5$ cells and $5\times10^5$ cells, respectively.

Accordingly, it was considered that culture of macrophage with the SW1990 mock cell line, in which MUC5AC was expressed, promoted PGE2 production by the macrophage, and caused the immune suppression. On the other hand, it was considered that the SW1990 si cell line, in which MUC5AC is not expressed, did not cause immune suppression, and suppressed proliferation of the SW1990 si cell line.

Example 11

Figure 11:
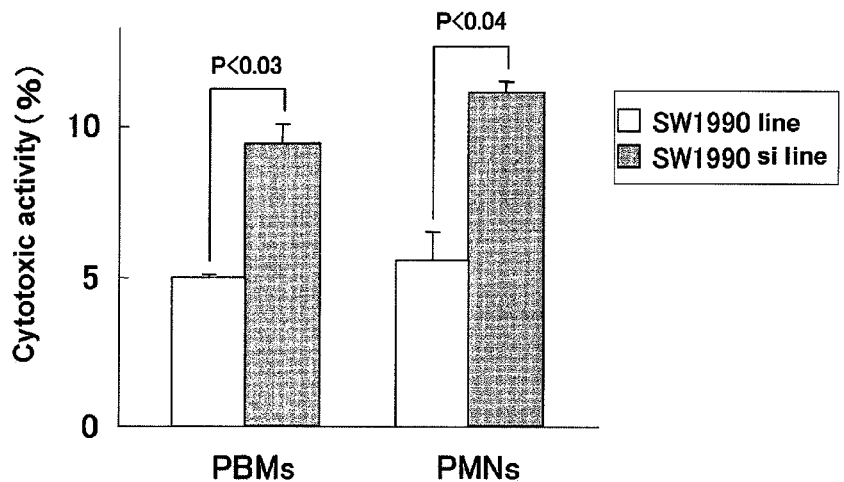
FIG. 11 is a graph showing the cytotoxic activity of mononuclear cells or polynuclear cells against SW1990 si cell line (MUC5AC knock-down cell line) and SW1990 mock cell line which are used as a target cells.

Cytotoxic Activity of Mononuclear Cell and Polynuclear Cell for the SW1990 si Cell Line In this Example 11, cytotoxic activity of healthy human peripheral blood against the SW1990 si cell as a target cell line was investigated using the $^{51}Cr$ release method. The mock cell line or si cell line (target cell), which were labeled with $10^3$ cells/well $^{51}Cr$, and $2.5\times10^4$ cells/well of mononuclear cell or polynuclear cell (effector cell) were co-cultured. After 24 hours, $^{51}Cr$ released from the target cell in the culture supernatant was measured. As a result, it was found that both of mononuclear cell and polynuclear cell showed stronger cytotoxic activity against the SW1990 si cell line, than against the SW1990 mock cell line. In other words, it was found that cytotoxic activity of the mononuclear cell and polynuclear cell is enhanced for the SW1990 si cell line in which MUC5AC expression is decreased by siRNA (FIG. 11).

Example 12

Isolation and Purification of MUC5AC from MUC5AC Expression Cell

The SW1990 cell line was collected by centrifugation, and the cell component was extracted using RIPA buffer (manufactured by Santa Cruz Biotechnology). The cell extraction liquid derived from the SW1990 cell line was concentrated with an ultrafiltration membrane (MW: 100,000), and then fractionation was performed with Sephacryl S-200 column, Sephacryl S-400 column, and Sepharose 4B column. Fractionation of MUC5AC was performed by ELISA using anti-MUC5AC antibody, anti-sialyl Tn antibody and anti-sialyl-Lewis A antibody and comparison to the chromatograph of the si cell line, to give MUC5AC of about 95% purity.

Example 13

Suppression of Mitogen Activity by MUC5AC

C3H/HeN-derived spleen cells were hemolyzed, and then suspended in RPMI medium (10% FBS, $5\times10^{-5}M$ mercaptoethanol) at $5\times10^6$ cells/mL, and dispersed to a 96 well plate by 100 μL ($5\times10^5$ cells/well). 5 μg/mL of Concanavalin A (ConA) as mitogen, and MUC5AC or cyclosporine A in various concentrations were added to each well, and a final volume in each well was set to 200 μL. The 96-well plate was cultured at 37° C. for 48 hours in an incubator kept at 100% humidity, 5% carbon dioxide and 95% air. The cell number was measured by MTT assay. As results, MUC5AC concentration-dependently suppressed the mitogen activity of the lymphocyte. Considering that the molecular weight of cyclosporine A is about 1200 and the molecular weight of MUC5AC is several millions to 10 millions, it was considered that the immune suppressive effect of MUC5AC is comparable to that of cyclosporine A.

INDUSTRIAL APPLICABILITY

The pharmaceutical composition of the present invention can be used for treatment and prevention of cancer in particular pancreatic cancer, and asthma.

Although the present invention has been described with reference to specific embodiments, various changes and modifications obvious to those skilled in the art are possible without departing from the scope of the appended claims.

The invention claimed is:

1. A small interfering RNA (siRNA) molecule that directs cleavage of mRNA of mucin subtype 5 AC via RNA interference, wherein a target mRNA region of the RNA interference is selected from the group consisting of an mRNA region consisting of a nucleotide sequence of SEQ ID NO:1, an mRNA region consisting of a nucleotide sequence of SEQ ID NO:3, an mRNA region consisting of a nucleotide sequence of SEQ ID NO:5, an mRNA region consisting of a nucleotide sequence of SEQ ID NO:7, an mRNA region consisting of a nucleotide sequence of SEQ ID NO:9, an mRNA region consisting of a nucleotide sequence of SEQ ID NO:11, an mRNA region consisting of a nucleotide sequence of SEQ ID NO:16, and an mRNA region consisting of a nucleotide sequence of SEQ ID NO:21.

2. The siRNA molecule according to claim 1, wherein the siRNA has a double-stranded RNA of 15 to 40 nucleotides in length.

3. The siRNA molecule according to claim 1, wherein the antisense RNA of the double-stranded RNA section comprises an RNA section consisting of a nucleotide sequence complementary to the nucleotide sequence of the target mRNA region, or an RNA section consisting of a nucleotide sequence in which 1 to 9 nucleotides are deleted, substituted, and/or added in one or more portions of the nucleotide sequence complementary to the nucleotide sequence of the target mRNA region.

4. The siRNA molecule according to claim 1, wherein the antisense RNA of the double-stranded RNA section comprises an RNA section consisting of the sequential nine or more nucleotide sequence in the nucleotide sequence complementary to the nucleotide sequence of the target mRNA region.

5. The siRNA molecule according to claim 1, wherein the antisense RNA of the double-stranded RNA section is selected from the group consisting of an RNA consisting of a nucleotide sequence of SEQ ID NO:2, an RNA consisting of a nucleotide sequence of SEQ ID NO:4, an RNA consisting of a nucleotide sequence of SEQ ID NO:6, an RNA consisting of a nucleotide sequence of SEQ ID NO:8, an RNA consisting of a nucleotide sequence of SEQ ID NO:10, an RNA consisting of a nucleotide sequence of SEQ ID NO:12, an RNA consisting of a nucleotide sequence of SEQ ID NO:17, and an RNA consisting of a nucleotide sequence of SEQ ID NO:22.

6. The siRNA molecule according to claim 1, wherein the siRNA is
   (a) a shRNA in which the two RNA strands constituting the double-stranded RNA section are connected with a RNA section which is capable of forming a hairpin loop,
   (b) a double-stranded nucleotide the ends of which are blunt ends, or
   (c) a double-stranded nucleotide in which the one or two ends thereof are protruding ends that are attached to a deoxyribonucleotide or a ribonucleotide on one or both 3'-ends of the two RNA strands constituting the double-stranded RNA section.

7. A DNA comprising a DNA section encoding the siRNA molecule according to claim 1, a promoter region at the 5'-terminus of the DNA section which is capable of controlling transcription of the DNA section, and a terminator region at the 3'-terminus of the DNA section.

8. A vector comprising the DNA according to claim 7.

9. A pharmaceutical composition comprising at least one component as an active ingredient selected from the group consisting of the siRNA molecule according to claim 1, the DNA according to claim 7, and the vector according to claim 8.

10. The pharmaceutical composition according to claim 9, for treating a disease involving an overexpression of mucin subtype 5 AC.

11. The pharmaceutical composition according to claim 10, wherein the disease involving an overexpression of mucin subtype 5 AC is pancreatic cancer or asthma.

12. A method for treating a disease involving an overexpression of mucin subtype 5 AC, comprising administrating to a patient in need of such treatment a therapeutically effective amount of at least one component selected from the group consisting of the siRNA molecule according to claim 1, the DNA according to claim 7, and the vector according to claim 8, wherein the disease involving an overexpression of mucin subtype 5 AC is pancreatic cancer or asthma.

13. The siRNA molecule according to claim 1, for treatment of a disease involving an overexpression of mucin subtype 5 AC, wherein the disease involving an overexpression of mucin subtype 5 AC is pancreatic cancer or asthma.

14. The DNA according to claim 7, for treatment of a disease involving an overexpression of mucin subtype 5 AC, wherein the disease involving an overexpression of mucin subtype 5 AC is pancreatic cancer or asthma.

15. The vector according to claim 8, for treatment of a disease involving an overexpression of mucin subtype 5 AC, wherein the disease involving an overexpression of mucin subtype 5 AC is pancreatic cancer or asthma.

16. A cell wherein a gene expression of mucin subtype 5 AC is knocked down by the siRNA molecule defined in claim 1.

* * * * *

SEQUENCE LISTING

<160> NUMBER OF SEQ ID NOS: 46

<210> SEQ ID NO 1
<211> LENGTH: 19
<212> TYPE: RNA
<213> ORGANISM: Artificial
<220> FEATURE:
<223> OTHER INFORMATION: synthetic target mRNA region 1 base sequence,
      siRNA-1s base sequence, sense strand siRNA for MUC5AC

<400> SEQUENCE: 1
ggagccugau cauccagca                                                    19

<210> SEQ ID NO 2
<211> LENGTH: 19
<212> TYPE: RNA
<213> ORGANISM: Artificial
<220> FEATURE:
<223> OTHER INFORMATION: synthetic siRNA-1as base sequence, antisense
      strand siRNA for MUC5AC

<400> SEQUENCE: 2
ugcuggauga ucaggcucc                                                    19

<210> SEQ ID NO 3
<211> LENGTH: 19
<212> TYPE: RNA
<213> ORGANISM: Artificial
<220> FEATURE:
<223> OTHER INFORMATION: synthetic target mRNA region 2 base sequence,
      siRNA-2s base sequence, sense strand siRNA for MUC5AC

<400> SEQUENCE: 3
gcaggcacuu cucccagga                                                    19

<210> SEQ ID NO 4
<211> LENGTH: 19
<212> TYPE: RNA
<213> ORGANISM: Artificial
<220> FEATURE:
<223> OTHER INFORMATION: synthetic siRNA-2as base sequence, antisense
      strand siRNA for MUC5AC

<400> SEQUENCE: 4
uccugggaga agugccugc                                                    19

<210> SEQ ID NO 5
<211> LENGTH: 19
<212> TYPE: RNA
<213> ORGANISM: Artificial
<220> FEATURE:
<223> OTHER INFORMATION: synthetic target mRNA region 3 base sequence,
      siRNA-3s base sequence, sense strand siRNA for MUC5AC

<400> SEQUENCE: 5
gcagugccuu cacuguacu                                                    19

<210> SEQ ID NO 6
<211> LENGTH: 19
<212> TYPE: RNA
<213> ORGANISM: Artificial
<220> FEATURE:
<223> OTHER INFORMATION: synthetic siRNA-3as base sequence, antisense
      strand siRNA for MUC5AC

<400> SEQUENCE: 6

-continued aguacaguga aggcacugc                                                    19

<210> SEQ ID NO 7
<211> LENGTH: 19
<212> TYPE: RNA
<213> ORGANISM: Artificial
<220> FEATURE:
<223> OTHER INFORMATION: synthetic target mRNA region 4 base sequence,
      siRNA-4s base sequence, sense strand siRNA for MUC5AC

<400> SEQUENCE: 7
acaccaagcu gacacccau                                                    19

<210> SEQ ID NO 8
<211> LENGTH: 19
<212> TYPE: RNA
<213> ORGANISM: Artificial
<220> FEATURE:
<223> OTHER INFORMATION: synthetic siRNA-4as base sequence, antisense
      strand siRNA for MUC5AC

<400> SEQUENCE: 8
auggguguca gcuuggugu                                                    19

<210> SEQ ID NO 9
<211> LENGTH: 19
<212> TYPE: RNA
<213> ORGANISM: Artificial
<220> FEATURE:
<223> OTHER INFORMATION: synthetic target mRNA region 5 base sequence,
      siRNA-5s base sequence, sense strand siRNA for MUC5AC

<400> SEQUENCE: 9
cccucaaccu ucuucauca                                                    19

<210> SEQ ID NO 10
<211> LENGTH: 19
<212> TYPE: RNA
<213> ORGANISM: Artificial
<220> FEATURE:
<223> OTHER INFORMATION: synthetic siRNA-5as base sequence, antisense
      strand siRNA for MUC5AC

<400> SEQUENCE: 10
ugaugaagaa gguugaggg                                                    19

<210> SEQ ID NO 11
<211> LENGTH: 19
<212> TYPE: RNA
<213> ORGANISM: Artificial
<220> FEATURE:
<223> OTHER INFORMATION: synthetic target mRNA region 6 base sequence,
      siRNA-6s base sequence, sense strand siRNA for MUC5AC

<400> SEQUENCE: 11
uuugagagac gaaggauac                                                    19

<210> SEQ ID NO 12
<211> LENGTH: 19
<212> TYPE: RNA
<213> ORGANISM: Artificial
<220> FEATURE:
<223> OTHER INFORMATION: synthetic siRNA-6as base sequence, antisense
      strand siRNA for MUC5AC

<400> SEQUENCE: 12
guauccuucg ucucucaaa                                                    19

<210> SEQ ID NO 13
<211> LENGTH: 64
<212> TYPE: DNA
<213> ORGANISM: Artificial
<220> FEATURE:
<223> OTHER INFORMATION: synthetic sense strand shDNA6-1 of short
      hairpin RNA shRNA6, siRNA for MUC5AC

<400> SEQUENCE: 13
gatccgtttg agagacgaag gatacttcaa gagagtatcc ttcgtctctc aaattttttg    60
gaaa                                                                 64

<210> SEQ ID NO 14
<211> LENGTH: 64
<212> TYPE: DNA
<213> ORGANISM: Artificial
<220> FEATURE:
<223> OTHER INFORMATION: synthetic antisense strand shDNA6-2 of short
      hairpin RNA shRNA6, siRNA for MUC5AC

<400> SEQUENCE: 14
agcttttcca aaaattga gagacgaagg atactctctt gaagtatcct tcgtctctca    60
aacg                                                                 64

<210> SEQ ID NO 15
<211> LENGTH: 47
<212> TYPE: RNA
<213> ORGANISM: Artificial
<220> FEATURE:
<223> OTHER INFORMATION: synthetic short hairpin RNA shRNA6, siRNA for
      MUC5AC

<400> SEQUENCE: 15
uuugagagac gaaggauacu ucaagagagu auccuucguc ucucaaa                 47

<210> SEQ ID NO 16
<211> LENGTH: 19
<212> TYPE: RNA
<213> ORGANISM: Artificial
<220> FEATURE:
<223> OTHER INFORMATION: synthetic target mRNA region 7 base sequence,
      siRNA-7s base sequence, sense strand siRNA for MUC5AC

<400> SEQUENCE: 16
ggaaaccuac aacaacauc                                                19

<210> SEQ ID NO 17
<211> LENGTH: 19
<212> TYPE: RNA
<213> ORGANISM: Artificial
<220> FEATURE:
<223> OTHER INFORMATION: synthetic siRNA-7as base sequence, antisense
      strand siRNA for MUC5AC

<400> SEQUENCE: 17
gauguuguug uagguuucc                                                19

<210> SEQ ID NO 18
<211> LENGTH: 63
<212> TYPE: DNA
<213> ORGANISM: Artificial
<220> FEATURE:
<223> OTHER INFORMATION: synthetic sense strand shDNA7-1 of short
      hairpin RNA shRNA7, siRNA for MUC5AC

<400> SEQUENCE: 18

```
gatccggaaa cctacaacaa catcttcaag agagatgttg ttgtaggttt ccttttttgg      60
aaa                                                                    63
```

<210> SEQ ID NO 19
<211> LENGTH: 63
<212> TYPE: DNA
<213> ORGANISM: Artificial
<220> FEATURE:
<223> OTHER INFORMATION: synthetic antisense strand shDNA7-2 of short
      hairpin RNA shRNA7, siRNA for MUC5AC

<400> SEQUENCE: 19

```
agcttttcca aaaaggaaa cctacaacaa catctctctt gaagatgttg ttgtaggttt      60
ccg                                                                    63
```

<210> SEQ ID NO 20
<211> LENGTH: 47
<212> TYPE: RNA
<213> ORGANISM: Artificial
<220> FEATURE:
<223> OTHER INFORMATION: synthetic short hairpin RNA shRNA7, siRNA for
      MUC5AC

<400> SEQUENCE: 20

```
ggaaaccuac aacaacaucu ucaagagaga uguuguugua gguuucc                    47
```

<210> SEQ ID NO 21
<211> LENGTH: 19
<212> TYPE: RNA
<213> ORGANISM: Artificial
<220> FEATURE:
<223> OTHER INFORMATION: synthetic target mRNA region 8 base sequence,
      siRNA-8s base sequence, sense strand siRNA for MUC5AC

<400> SEQUENCE: 21

```
caucaacauc auccauguc                                                   19
```

<210> SEQ ID NO 22
<211> LENGTH: 19
<212> TYPE: RNA
<213> ORGANISM: Artificial
<220> FEATURE:
<223> OTHER INFORMATION: synthetic siRNA-8as base sequence, antisense
      strand siRNA for MUC5AC

<400> SEQUENCE: 22

```
gacauggaug auguugaug                                                   19
```

<210> SEQ ID NO 23
<211> LENGTH: 64
<212> TYPE: DNA
<213> ORGANISM: Artificial
<220> FEATURE:
<223> OTHER INFORMATION: synthetic sense strand shDNA8-1 of short
      hairpin RNA shRNA8, siRNA for MUC5AC

<400> SEQUENCE: 23

```
gatccgcatc aacatcatcc atgtcttcaa gagagacatg gatgatgttg atgttttttg      60
gaaa                                                                   64
```

<210> SEQ ID NO 24
<211> LENGTH: 64
<212> TYPE: DNA
<213> ORGANISM: Artificial
<220> FEATURE:
<223> OTHER INFORMATION: synthetic antisense strand shDNA8-2 of short hairpin RNA shRNA8, siRNA for MUC5AC

<400> SEQUENCE: 24
agcttttcca aaaacatca acatcatcca tgtctctctt gaagacatgg atgatgttga    60
tgcg    64

<210> SEQ ID NO 25
<211> LENGTH: 47
<212> TYPE: RNA
<213> ORGANISM: Artificial
<220> FEATURE:
<223> OTHER INFORMATION: synthetic short hairpin RNA shRNA8, siRNA for
      MUC5AC

<400> SEQUENCE: 25
caucaacauc auccaugucu ucaagagaga cauggaugau guugaug    47

<210> SEQ ID NO 26
<211> LENGTH: 21
<212> TYPE: DNA
<213> ORGANISM: Artificial
<220> FEATURE:
<223> OTHER INFORMATION: synthetic MUC5AC mRNA specific RT-PCR sense
      primer

<400> SEQUENCE: 26
gccaccgctg cggccttctt c    21

<210> SEQ ID NO 27
<211> LENGTH: 21
<212> TYPE: DNA
<213> ORGANISM: Artificial
<220> FEATURE:
<223> OTHER INFORMATION: synthetic MUC5AC mRNA specific RT-PCR antisense
      primer

<400> SEQUENCE: 27
gtgcacgtag gaggacagcg c    21

<210> SEQ ID NO 28
<211> LENGTH: 22
<212> TYPE: DNA
<213> ORGANISM: Artificial
<220> FEATURE:
<223> OTHER INFORMATION: synthetic GAPDH mRNA specific RT-PCR sense
      primer

<400> SEQUENCE: 28
tcctgcacca ccaactgctt ag    22

<210> SEQ ID NO 29
<211> LENGTH: 22
<212> TYPE: DNA
<213> ORGANISM: Artificial
<220> FEATURE:
<223> OTHER INFORMATION: synthetic GAPDH mRNA specific RT-PCR antisense
      primer

<400> SEQUENCE: 29
tcttactcct tggaggccat gt    22

<210> SEQ ID NO 30
<211> LENGTH: 10
<212> TYPE: RNA
<213> ORGANISM: Artificial
<220> FEATURE:
<223> OTHER INFORMATION: synthetic siRNA short hairpin RNA (shRNA)

-continued hairpin loop sequence

<400> SEQUENCE: 30
cuuccuguca                                                                 10

<210> SEQ ID NO 31
<211> LENGTH: 21
<212> TYPE: DNA
<213> ORGANISM: Artificial
<220> FEATURE:
<223> OTHER INFORMATION: synthetic oh-siRNA1 sense strand siRNA with 3'
      end overhang for MUC5AC target mRNA region 1
<220> FEATURE:
<223> OTHER INFORMATION: Description of Combined DNA/RNA Molecule:
      synthetic oh-siRNA1 sense strand siRNA with 3' end overhang for
      MUC5AC target mRNA region 1

<400> SEQUENCE: 31
ggagccugau cauccagcat t                                                    21

<210> SEQ ID NO 32
<211> LENGTH: 21
<212> TYPE: DNA
<213> ORGANISM: Artificial
<220> FEATURE:
<223> OTHER INFORMATION: synthetic oh-siRNA1 antisense strand siRNA with
      3' end overhang for MUC5AC target mRNA region 1
<220> FEATURE:
<223> OTHER INFORMATION: Description of Combined DNA/RNA Molecule:
      synthetic oh-siRNA1 antisense strand siRNA with 3' end overhang
      for MUC5AC target mRNA region 1

<400> SEQUENCE: 32
ugcuggauga ucaggcucct t                                                    21

<210> SEQ ID NO 33
<211> LENGTH: 21
<212> TYPE: DNA
<213> ORGANISM: Artificial
<220> FEATURE:
<223> OTHER INFORMATION: synthetic oh-siRNA2 sense strand siRNA with 3'
      end overhang for MUC5AC target mRNA region 2
<220> FEATURE:
<223> OTHER INFORMATION: Description of Combined DNA/RNA Molecule:
      synthetic oh-siRNA2 sense strand siRNA with 3' end overhang for
      MUC5AC target mRNA region 2

<400> SEQUENCE: 33
gcaggcacuu cucccaggat t                                                    21

<210> SEQ ID NO 34
<211> LENGTH: 21
<212> TYPE: DNA
<213> ORGANISM: Artificial
<220> FEATURE:
<223> OTHER INFORMATION: synthetic oh-siRNA2 antisense strand siRNA with
      3' end overhang for MUC5AC target mRNA region 2
<220> FEATURE:
<223> OTHER INFORMATION: Description of Combined DNA/RNA Molecule:
      synthetic oh-siRNA2 antisense strand siRNA with 3' end overhang
      for MUC5AC target mRNA region 2

<400> SEQUENCE: 34
uccugggaga agugccugct t                                                    21

<210> SEQ ID NO 35
<211> LENGTH: 21
<212> TYPE: DNA
<213> ORGANISM: Artificial
<220> FEATURE:

```
<223> OTHER INFORMATION: synthetic oh-siRNA3 sense strand siRNA with 3'
      end overhang for MUC5AC target mRNA region 3
<220> FEATURE:
<223> OTHER INFORMATION: Description of Combined DNA/RNA Molecule:
      synthetic oh-siRNA3 sense strand siRNA with 3' end overhang for
      MUC5AC target mRNA region 3

<400> SEQUENCE: 35
gcagugccuu cacuguacut t                                              21

<210> SEQ ID NO 36
<211> LENGTH: 21
<212> TYPE: DNA
<213> ORGANISM: Artificial
<220> FEATURE:
<223> OTHER INFORMATION: synthetic oh-siRNA3 antisense strand siRNA with
      3' end overhang for MUC5AC target mRNA region 3
<220> FEATURE:
<223> OTHER INFORMATION: Description of Combined DNA/RNA Molecule:
      synthetic oh-siRNA3 antisense strand siRNA with 3' end overhang
      for MUC5AC target mRNA region 3

<400> SEQUENCE: 36
aguacaguga aggcacugct t                                              21

<210> SEQ ID NO 37
<211> LENGTH: 21
<212> TYPE: DNA
<213> ORGANISM: Artificial
<220> FEATURE:
<223> OTHER INFORMATION: synthetic oh-siRNA4 sense strand siRNA with 3'
      end overhang for MUC5AC target mRNA region 4
<220> FEATURE:
<223> OTHER INFORMATION: Description of Combined DNA/RNA Molecule:
      synthetic oh-siRNA4 sense strand siRNA with 3' end overhang for
      MUC5AC target mRNA region 4

<400> SEQUENCE: 37
acaccaagcu gacacccaut t                                              21

<210> SEQ ID NO 38
<211> LENGTH: 21
<212> TYPE: DNA
<213> ORGANISM: Artificial
<220> FEATURE:
<223> OTHER INFORMATION: synthetic oh-siRNA4 antisense strand siRNA with
      3' end overhang for MUC5AC target mRNA region 4
<220> FEATURE:
<223> OTHER INFORMATION: Description of Combined DNA/RNA Molecule:
      synthetic oh-siRNA4 antisense strand siRNA with 3' end overhang
      for MUC5AC target mRNA region 4

<400> SEQUENCE: 38
auggguguca gcuuggugut t                                              21

<210> SEQ ID NO 39
<211> LENGTH: 21
<212> TYPE: DNA
<213> ORGANISM: Artificial
<220> FEATURE:
<223> OTHER INFORMATION: synthetic oh-siRNA5 sense strand siRNA with 3'
      end overhang for MUC5AC target mRNA region 5
<220> FEATURE:
<223> OTHER INFORMATION: Description of Combined DNA/RNA Molecule:
      synthetic oh-siRNA5 sense strand siRNA with 3' end overhang for
      MUC5AC target mRNA region 5

<400> SEQUENCE: 39
cccucaaccu ucuucaucat t                                              21
```

```
<210> SEQ ID NO 40
<211> LENGTH: 21
<212> TYPE: DNA
<213> ORGANISM: Artificial
<220> FEATURE:
<223> OTHER INFORMATION: synthetic oh-siRNA5 antisense strand siRNA with
      3' end overhang for MUC5AC target mRNA region 5
<220> FEATURE:
<223> OTHER INFORMATION: Description of Combined DNA/RNA Molecule:
      synthetic oh-siRNA5 antisense strand siRNA with 3' end overhang
      for MUC5AC target mRNA region 5

<400> SEQUENCE: 40
ugaugaagaa gguugagggt t                                              21

<210> SEQ ID NO 41
<211> LENGTH: 21
<212> TYPE: DNA
<213> ORGANISM: Artificial
<220> FEATURE:
<223> OTHER INFORMATION: synthetic oh-siRNA6 sense strand siRNA with 3'
      end overhang for MUC5AC target mRNA region 6
<220> FEATURE:
<223> OTHER INFORMATION: Description of Combined DNA/RNA Molecule:
      synthetic oh-siRNA6 sense strand siRNA with 3' end overhang for
      MUC5AC target mRNA region 6

<400> SEQUENCE: 41
uuugagagac gaaggauact t                                              21

<210> SEQ ID NO 42
<211> LENGTH: 21
<212> TYPE: DNA
<213> ORGANISM: Artificial
<220> FEATURE:
<223> OTHER INFORMATION: synthetic oh-siRNA6 antisense strand siRNA with
      3' end overhang for MUC5AC target mRNA region 6
<220> FEATURE:
<223> OTHER INFORMATION: Description of Combined DNA/RNA Molecule:
      synthetic oh-siRNA6 antisense strand siRNA with 3' end overhang
      for MUC5AC target mRNA region 6

<400> SEQUENCE: 42
guauccuucg ucucucaaat t                                              21

<210> SEQ ID NO 43
<211> LENGTH: 21
<212> TYPE: DNA
<213> ORGANISM: Artificial
<220> FEATURE:
<223> OTHER INFORMATION: synthetic oh-siRNA7 sense strand siRNA with 3'
      end overhang for MUC5AC target mRNA region 7
<220> FEATURE:
<223> OTHER INFORMATION: Description of Combined DNA/RNA Molecule:
      synthetic oh-siRNA7 sense strand siRNA with 3' end overhang for
      MUC5AC target mRNA region 7

<400> SEQUENCE: 43
ggaaaccuac aacaacauct t                                              21

<210> SEQ ID NO 44
<211> LENGTH: 21
<212> TYPE: DNA
<213> ORGANISM: Artificial
<220> FEATURE:
<223> OTHER INFORMATION: synthetic oh-siRNA7 antisense strand siRNA with
      3' end overhang for MUC5AC target mRNA region 7
<220> FEATURE:
<223> OTHER INFORMATION: Description of Combined DNA/RNA Molecule:
      synthetic oh-siRNA7 antisense strand siRNA with 3' end overhang
      for MUC5AC target mRNA region 7
```

```
-continued

<400> SEQUENCE: 44
gauguuguug uagguuucct t                                              21

<210> SEQ ID NO 45
<211> LENGTH: 21
<212> TYPE: DNA
<213> ORGANISM: Artificial
<220> FEATURE:
<223> OTHER INFORMATION: synthetic oh-siRNA8 sense strand siRNA with 3'
      end overhang for MUC5AC target mRNA region 8
<220> FEATURE:
<223> OTHER INFORMATION: Description of Combined DNA/RNA Molecule:
      synthetic oh-siRNA8 sense strand siRNA with 3' end overhang for
      MUC5AC target mRNA region 8

<400> SEQUENCE: 45
caucaacauc auccauguct t                                              21

<210> SEQ ID NO 46
<211> LENGTH: 21
<212> TYPE: DNA
<213> ORGANISM: Artificial
<220> FEATURE:
<223> OTHER INFORMATION: synthetic oh-siRNA8 antisense strand siRNA with
      3' end overhang for MUC5AC target mRNA region 8
<220> FEATURE:
<223> OTHER INFORMATION: Description of Combined DNA/RNA Molecule:
      synthetic oh-siRNA8 antisense strand siRNA with 3' end overhang
      for MUC5AC target mRNA region 8

<400> SEQUENCE: 46
gacauggaug auguugaugt t                                              21
```